United States Patent [19]

Tamaru et al.

[11] Patent Number: 5,302,739
[45] Date of Patent: Apr. 12, 1994

[54] PYRIMIDINE OR TRIAZINE DERIVATIVES

[75] Inventors: Masatoshi Tamaru, Kakegawa; Norihiro Kawamura, Shizuoka; Masahiro Sato, Fukuroi; Fumiaki Takabe, Shizuoka; Shigehiko Tachikawa, Shizuoka; Ryo Yoshida, Shizuoka, all of Japan

[73] Assignees: Kumiai Chemical Industry Co.; Ihara Chemical Industry Co., Ltd., both of Tokyo, Japan

[21] Appl. No.: 968,316

[22] Filed: Oct. 29, 1992

Related U.S. Application Data

[62] Division of Ser. No. 845,658, Mar. 4, 1992, which is a division of Ser. No. 630,892, Dec. 20, 1990, Pat. No. 5,118,339.

[30] Foreign Application Priority Data

Dec. 28, 1989 [JP] Japan .................. 1-343287
Oct. 5, 1990 [JP] Japan .................. 2-120678

[51] Int. Cl.$^5$ .......................................... C07C 229/38
[52] U.S. Cl. ..................... 558/257; 560/12; 560/18; 560/34; 560/35; 560/42; 562/26; 562/430; 562/432; 562/440; 564/162; 564/167
[58] Field of Search ............ 558/257; 560/12, 18, 560/34, 35, 42; 562/26, 430, 432, 440; 564/162, 167

[56] References Cited

U.S. PATENT DOCUMENTS 5,118,339 6/1992 Tamaru et al. .............. 544/316 X
5,242,895 9/1993 Tamaru et al. .............. 504/277

FOREIGN PATENT DOCUMENTS 0287079 10/1988 European Pat. Off. .
2186256 1/1974 France .

OTHER PUBLICATIONS

Rheinheimer et al, Chemical Abstracts, vol. 117 (1992) 7950c.
Derwent Japanese Patent Reports, vol. 13, No. 63 (C-568)[3411], Feb. 13, 1989; & JP-A-63 258 463 (Kurniori) *abstract*.

Primary Examiner—Richard L. Raymond
Attorney, Agent, or Firm—Oblon, Spivak, McClelland, Maier & Neustadt

[57] ABSTRACT

Compounds of the formula $$\begin{array}{c} R^2-N \\ \parallel \\ R^1-C \end{array} \text{-Ar-} \begin{array}{c} COR \\ Y^1H \end{array}$$

as intermediates for the preparation of pyrimidine or triazine herbicides.

3 Claims, No Drawings

PYRIMIDINE OR TRIAZINE DERIVATIVES

This is a division of application Ser. No. 07/845,658, filed Mar. 4, 1992, which is a division of Ser. No. 07/630,892, filed on Dec. 20, 1990, which is now U.S. Pat. No. 5,118,339.

The present invention relates to novel pyrimidine or triazine derivatives and their salts. More particularly, the present invention relates to pyrimidine or triazine derivatives expressed by the general formula [I] as described below, and also relates to herbicidal compositions containing said pyrimidine or triazine derivatives or their salts as active ingredients, which can be applied to paddy fields, upland fields or non-agricultural fields.

U.S. Pat. No. 4,770,691 (Japanese Unexamined Patent Publication No. 174059/1987), U.S. Pat. No. 4,427,437 (Japanese Unexamined Patent Publication No. 55729/1979) and Agr. Biol. Chem., Vol. 30, No. 9, p.896 (1966) disclose that 2-phenoxypyrimidine derivatives have herbicidal activities.

However, the compounds disclosed in these patent specifications and references are not always satisfactory in respect of their herbicidal effects. The present inventors have conducted excessive researches with an aim to develop a further improved compound of the pyrimidine or triazine type compounds, and have found that the pyrimidine or triazine derivatives having substituents at the specific positions on a pyrimidine or triazine ring and a benzene ring exhibit excellent herbicidal activities against not only annular weeds but also perennial weeds and also have a high safety to crop plants, particularly to rice. The present invention has been accomplished on the basis of these discoveries.

The present invention provides a pyrimidine or triazine derivative and its salt, said pyrimidine or triazine derivative having the general formula [I]:

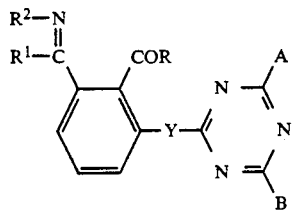

wherein R represents a group of the formula OR$^3$ {wherein R$^3$ represents a hydrogen atom, an alkyl group, preferably a C$_{1-8}$ alkyl group, more preferably a C$_{1-4}$ alkyl group (which may be substituted with a halogen atom, a nitro group, a cyano group, an alkoxy group, preferably a C$_{1-8}$ alkoxy group, more preferably a C$_{1-4}$ alkoxy group, an alkylthio group, preferably a C$_{1-8}$ alkylthio group, more preferably a C$_{1-4}$ alkylthio group, an alkylsulfinyl group, preferably a C$_{1-8}$ alkylsulfinyl group, more preferably a C$_{1-4}$ alkylsulfinyl group, an alkylsulfonyl group, preferably a C$_{1-8}$ alkylsulfonyl group, more preferably a C$_{1-4}$ alkylsulfonyl group, a phenylthio group, a phenylsulfinyl group, a phenylsulfonyl group, a benzyloxy group, an acyloxy group, preferably a R'COO— (R'=C$_{1-8}$ alkyl), an alkoxycarbonyloxy group, preferably a C$_{1-8}$ alkoxycarbonyloxy group, an N,N-dialkylamino group, preferably an N,N-di-C$_{1-4}$ alkylamino group, or a phthalimidoyl group), an alkenyl group, preferably a C$_{2-8}$ alkenyl group, a halogen-substituted alkenyl group, preferably a halogen-substituted C$_{2-8}$ alkenyl group, an alkynyl group, preferably a C$_{2-8}$ alkynyl group, a halogen-substituted alkynyl group, preferably a halogen-substituted C$_{2-8}$ alkynyl group, a phenyl group (which may be substituted with a halogen atom, an alkyl group, preferably a C$_{1-6}$ alkyl group, or an alkoxy group, preferably a C$_{1-6}$ alkoxy group), a benzyl group (which may be substituted with a halogen atom, an alkyl group, preferably a C$_{1-8}$ alkyl group, or an alkoxy group, preferably a C$_{1-8}$ alkoxy group), an alkylideneamino group, preferably a C$_{1-4}$ alkylideneamino group, a cycloalkylideneamino group, preferably a C$_{4-6}$ cycloalkylideneamino group, a group of the formula

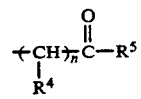

(wherein R$^4$ represents a hydrogen atom or an alkyl group, preferably a C$_{1-3}$ alkyl group, R$^5$ represents an alkyl group, preferably a C$_{1-8}$ alkyl group, a phenyl group (which may be substituted with a halogen atom, an alkyl group, preferably a C$_{1-6}$ alkyl group, or an alkoxy group, preferably a C$_{1-6}$ alkoxy group), an amino group, an alkylamino group, preferably a C$_{1-8}$ alkylamino group, or a dialkylamino group, preferably a di-C$_{1-4}$ alkylamino group, n represents an integer of 1 to 3), an alkali metal atom, an alkaline earth metal atom or {an organic amine cation}; a group of the formula SR$^6$ wherein R$^6$ represents a hydrogen atom, an alkyl group, preferably a C$_{1-8}$ alkyl group, a phenyl group (which may be substituted with a halogen atom, an alkyl group, preferably a C$_{1-6}$ alkyl group, or an alkoxy group, preferably a C$_{1-6}$ alkoxy group), a benzyl group (which may be substituted with a halogen atom, an alkyl group, preferably a C$_{1-6}$ alkyl group, or an alkoxy group, preferably a C$_{1-6}$ alkoxy group), an alkenyl group, preferably a C$_{2-8}$ alkenyl group, a halogen-substituted alkenyl group, preferably a halogen-substituted C$_{2-8}$ alkenyl group, an alkynyl group, preferably a C$_{2-8}$ alkynyl group, or a halogen-substituted alkynyl group, preferably a halogen-substituted C$_{2-8}$ alkynyl group}; a group of the formula

{wherein R$^7$ and R$^8$ may be the same or different and represent a hydrogen atom, an alkyl group, preferably a C$_{1-8}$ alkyl group, an alkoxy group, preferably a C$_{1-8}$ alkoxy group, or a phenyl group (which may be substituted with a halogen atom, an alkyl group, preferably a C$_{1-6}$ alkyl group, or an alkoxy group, preferably a C$_{1-6}$ alkoxy group)}; or an imidazolyl group;

R$^1$ represents a hydrogen atom, an alkyl group, preferably a C$_{1-8}$ alkyl group (which may be substituted with a halogen atom, an alkoxy group, preferably a C$_{1-8}$ alkoxy group, an alkylthio group, preferably a C$_{1-8}$ alkylthio group, an alkylsulfinyl group, preferably a C$_{1-8}$ alkylsulfinyl group, an alkylsulfonyl group, preferably a C$_{1-8}$ alkylsulfonyl group, an acyl group, preferably an R"CO— (R"=C$_{1-6}$ alkyl, phenyl or benzyl), or a Cyano group), a phenyl group (which may be substituted with a halogen atom, an alkyl group, preferably a C$_{1-6}$ alkyl group, or an alkoxy group, preferably a C$_{1-6}$ alkoxy group) or a benzyl group (which may be substituted with a halogen atom, an alkyl group, preferably a $C_{1-6}$ alkyl group, or an alkoxy group, preferably a $C_{1-6}$ alkoxy group);

$R^2$ represents a hydroxyl group, an alkyl group, preferably a $C_{1-8}$ alkyl group (which may be substituted with one or two halogen atoms), an alkoxyalkyl group, preferably a $C_{1-8}$ alkoxyalkyl group, an alkenyl group, preferably a $C_{2-8}$ alkenyl group, an alkynyl group, preferably a $C_{2-8}$ alkynyl group, an alkoxy group, preferably a $C_{1-8}$ alkoxy group (which may be substituted with a halogen atom, a benzyloxy group, an alkoxycarbonyl group, preferably a $C_{1-8}$ alkoxycarbonyl group, a cycloalkyl group, preferably a $C_{3-7}$ cycloalkyl group, an acyl group, an N,N-dialkylamino group, preferably an N,N-di-$C_{1-4}$ alkylamino group, or an alkoxy group, preferably a $C_{1-8}$ alkoxy group), a phenyl group (which may be substituted with a halogen atom, an alkyl group, preferably a $C_{1-4}$ alkyl group, or an alkoxy group, preferably a $C_{1-4}$ alkoxy group), a phenoxy group (which may be substituted with a halogen atom, an alkyl group, preferably a $C_{1-4}$ alkyl group, or an alkoxy group, preferably a $C_{1-4}$ alkoxy group), an alkenyloxy group, preferably a $C_{1-8}$ alkenyloxy group (which may be substituted with one or two halogen atoms or a phenyl group), an alkynyloxy group, preferably a $C_{2-8}$ alkynyloxy group (which may be substituted with one or two halogen atoms or a phenyl group), a benzyloxy group (which may be substituted with a halogen atom, an alkyl group, preferably a $C_{1-4}$ alkyl group, or an alkoxy group, preferably a $C_{1-4}$ alkoxy group), a trimethylsilyloxy group, a cycloalkoxy group, preferably a $C_{3-7}$ cycloalkoxy group, a group of the formula

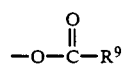

{wherein $R^9$ represents an alkyl group, preferably a $C_{1-8}$ alkyl group (which may be substituted with a halogen atom), a cycloalkyl group, preferably a $C_{3-7}$ cycloalkyl group, a phenyl group (which may be substituted with a halogen atom, an alkyl group, preferably a $C_{1-4}$ alkyl group, or an alkoxy group, preferably a $C_{1-4}$ alkoxy group), an alkoxy group, preferably a $C_{1-8}$ alkoxy group, or a group of the formula:

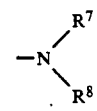

(wherein $R^7$ and $R^8$ are the same as defined above)}, a group of the formula

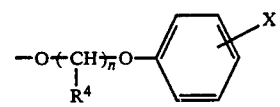

(wherein X represents a halogen atom, an alkyl group, preferably a $C_{1-4}$ alkyl group, or an alkoxy group, preferably a $C_{1-4}$ alkoxy group, n represents an integer of 1 to 3 and $R^4$ is the same as defined above), a phenylamino group, an alkoxycarbonylamino group, preferably a $C_{1-4}$ alkoxycarbonylamino group, or an alkylcarbonylamino group, preferably a $C_{1-4}$ alkylcarbonylamino group; A and B may be the same or different and represent an alkyl group, preferably a $C_{1-4}$ alkyl group, an alkoxy group, preferably a $C_{1-4}$ alkoxy group, a halogen atom, a halogen-substituted alkyl group, preferably a halogen-substituted $C_{1-4}$ alkyl group, a halogen-substituted alkoxy group, preferably a halogen-substituted $C_{1-4}$ alkoxy group, or a dialkylamino group, preferably a di-$C_{1-4}$ alkylamino group; Y represents an oxygen atom, a sulfur atom, an —NH— group or a group of the formula

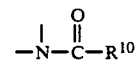

(wherein $R^{10}$ represents a hydrogen atom, an alkyl group, preferably a $C_{1-8}$ alkyl group, or an alkoxy group, preferably a $C_{1-8}$ alkoxy group); and Z represents a methine group or a nitrogen atom.

Typical examples of the compound expressed by the general formula [I] of the present invention are listed in the following Table 1.

TABLE 1

(I)

[Structure: R²-N=C(R¹)- and -COR groups on a benzene ring with -Y-C(=N-A)(N-B) linkage where N-substituents connect to Z]

| Compound No. | R | R¹ | R² | A | B | Y | Z | Physical properties: Melting point (°C.) or Refractive index ($n_D^{20}$) |
|---|---|---|---|---|---|---|---|---|
| 1 | OH | CH₃ | OCH₃ | OCH₃ | OCH₃ | O | CH | 125–127 |
| 2 | OH | CH₃ | OC₂H₅ | OCH₃ | OCH₃ | O | CH | 113–115 |
| 3 | OH | CH₃ | OC₃H₇-i | OCH₃ | OCH₃ | O | CH | 1.5380 |
| 4 | OCH₂—C₆H₅ | CH₃ | OCH₃ | OCH₃ | OCH₃ | O | CH | 1.5545 |
| 5 | OCH₂—C₆H₅ | CH₃ | OC₂H₅ | OCH₃ | OCH₃ | O | CH | 80–82 |
| 6 | OCH₂—C₆H₅ | CH₃ | OC₃H₇-i | OCH₃ | OCH₃ | O | CH | 1.5472 |
| 7 | OCH₂—C₆H₅ | CH₃ | OCH₂—C₆H₅ | OCH₃ | OCH₃ | O | CH | 1.5817 |
| 8 | OCH₃ | CH₃ | OH | OCH₃ | OCH₃ | O | CH | 131–132 |
| 9 | OCH₃ | CH₃ | OCH₃ | OCH₃ | OCH₃ | O | CH | 105–106 |
| 10 | OCH₃ | CH₃ | OCH₃ | OCH₃ | OCH₃ | O | CH | unmeasurable |
| 11 | OCH₃ | CH₃ | OC₂H₅ | OCH₃ | OCH₃ | O | CH | 93–95 |
| 12 | OCH₃ | CH₃ | OC₃H₇-i | OCH₃ | OCH₃ | O | CH | 74–75 |

TABLE 1-continued $$\begin{array}{c} R^2-N \\ R^1-C \end{array} \begin{array}{c} COR \\ \end{array} \begin{array}{c} A \\ N \\ Y \\ N \end{array} B \quad (I)$$

| Compound No. | R | R[1] | R[2] | A | B | Y | Z | Physical properties: Melting point (°C.) or Refractive index ($n_D^{20}$) |
|---|---|---|---|---|---|---|---|---|
| 13 | OCH$_3$ | CH$_3$ | OCH$_2$-C$_6$H$_5$ | OCH$_3$ | OCH$_3$ | O | CH | 1.5681 |
| 14 | OCH$_3$ | CH$_3$ | OCH$_2$CH=CH$_2$ | OCH$_3$ | OCH$_3$ | O | CH | 76–78 |
| 15 | OC$_2$H$_5$ | CH$_3$ | OCH$_3$ | OCH$_3$ | OCH$_3$ | O | CH | 65–68 |
| 16 | OC$_3$H$_7$ | CH$_3$ | OCH$_3$ | OCH$_3$ | OCH$_3$ | O | CH | 1.5449 |
| 17 | OC$_3$H$_7$-i | CH$_3$ | OCH$_3$ | OCH$_3$ | OCH$_3$ | O | CH | 1.5301 |
| 18 | OH | H | OCH$_3$ | OCH$_3$ | OCH$_3$ | O | CH | 109–111.5 |
| 19 | OCH$_3$ | H | OH | OCH$_3$ | OCH$_3$ | O | CH | 1.5558 |
| 20 | OCH$_3$ | H | OCH$_3$ | OCH$_3$ | OCH$_3$ | O | CH | 78–79 |
| 21 | OCH$_3$ | H | OC$_2$H$_5$ | OCH$_3$ | OCH$_3$ | O | CH | 1.5582 |
| 22 | OCH$_3$ | H | CH$_3$-CH(OCHCOOC$_2$H$_5$) | OCH$_3$ | OCH$_3$ | O | CH | 1.5261 |
| 23 | OCH$_3$ | H | OCH$_2$-C$_6$H$_5$ | OCH$_3$ | OCH$_3$ | O | CH | 1.5799 |
| 24 | OCH$_3$ | H | NH-C$_6$H$_5$ | OCH$_3$ | OCH$_3$ | O | CH | unmeasurable |
| 25 | OCH$_3$ | H | NHCOOCH$_3$ | OCH$_3$ | OCH$_3$ | O | CH | 108–109 |
| 26 | OCH$_3$ | H | NHCOOC$_2$H$_5$ | OCH$_3$ | OCH$_3$ | O | CH | 136–138 |
| 27 | OCH$_3$ | H | NHCOCH$_3$ | OCH$_3$ | OCH$_3$ | O | CH | 144–146 |

TABLE 1-continued (I)

$$\begin{array}{c}R^2-N\\ \parallel\\ R^1-C\end{array}\bigg\langle\begin{array}{c}COR\\ \\ \end{array}\bigg\rangle-Y\bigg\langle\begin{array}{c}N\\ \\ N\end{array}\bigg\rangle\begin{array}{c}A\\ \\ B\end{array}$$

| Compound No. | R | R[1] | R[2] | A | B | Y | Z | Physical properties: Melting point (°C.) or Refractive index ($n_D^{20}$) |
|---|---|---|---|---|---|---|---|---|
| 28 | OCH$_3$ | H | ⟨phenyl⟩ | OCH$_3$ | OCH$_3$ | O | CH | 122-124 |
| 29 | OC$_2$H$_5$ | H | OCH$_3$ | OCH$_3$ | OCH$_3$ | O | CH | 1.5449 |
| 30 | OC$_3$H$_7$-i | H | OCH$_3$ | OCH$_3$ | OCH$_3$ | O | CH | 1.5450 |
| 31 | OCH$_2$(CH$_2$)$_2$—CH$_2$OCH$_3$ | H | OCH$_3$ | OCH$_3$ | OCH$_3$ | O | CH | 1.5430 |
| 32 | OCH$_2$⟨phenyl⟩ | H | OCH$_3$ | OCH$_3$ | OCH$_3$ | O | CH | 1.5741 |
| 33 | OCH$_3$ | CH$_3$ | OCH$_3$ | OCH$_3$ | OCH$_3$ | S | CH | 1.5709 |
| 34 | OCH$_3$ | CH$_3$ | OC$_2$H$_5$ | OCH$_3$ | OCH$_3$ | S | CH | 62.5-64 |
| 35 | OCH$_3$ | H | ⟨O-phenyl⟩ | OCH$_3$ | OCH$_3$ | O | CH | 1.5849 |
| 36 | OCH$_3$ | CH$_3$ | OCH$_3$ | Cl | OCH$_3$ | O | CH | 110-113 |
| 37 | OCH$_3$ | CH$_3$ | OCH$_3$ | Cl | CH$_3$ | O | CH | 1.5587 |
| 38 | OCH$_3$ | CH$_3$ | OCH$_3$ | CH$_3$ | OCH$_3$ | O | CH | 126-129 |
| 39 | OCH$_3$ | CH$_3$ | OCH$_3$ | OC$_2$H$_5$ | OC$_2$H$_5$ | O | CH | 1.5342 |
| 40 | OCH$_3$ | CH$_3$ | OCH$_3$ | CH$_3$ | CH$_3$ | O | CH | 79-80 |
| 41 | OCH$_3$ | CH$_3$ | OCH$_3$ | OCH$_3$ | OCH$_3$ | O | N | 131-135 |
| 42 | OCH$_2$⟨phenyl⟩ | CH$_3$ | ⟨O-phenyl⟩ | OCH$_3$ | OCH$_3$ | O | CH | 1.5740 |

TABLE 1-continued

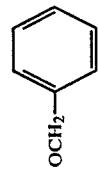

(I)

| Compound No. | R | R¹ | R² | A | B | Y | Z | Physical properties: Melting point (°C.) or Refractive index ($n_D^{20}$) |
|---|---|---|---|---|---|---|---|---|
| 43 | OCH₃ | CH₃ | OC₃H₇ | OCH₃ | OCH₃ | O | CH | 73-76 |
| 44 | OCH₂—⌬ | CH₃ | OC₃H₇ | OCH₃ | OCH₃ | O | CH | 65-66 |
| 45 | OH | CH₃ | OC₃H₇ | OCH₃ | OCH₃ | O | CH | 1.5112 |
| 46 | OCH₃ | CH₃ | OCH₃ | OCH₃ | OCH₃ | O | CH | 82-84 |
| 47 | OCH₃ | CH₃ | OCH₃ | OCH₃ | OCH₃ | NH | CH | 139-141 |
| 48 | OCH₂OC₂H₅ | CH₃ | OCH₃ | OCH₃ | OCH₃ | NH | CH | 1.5290 |
| 49 | ONa | CH₃ | OCH₃ | OCH₃ | OCH₃ | O | CH | 138-150 |
| 50 | OCH₃ | CH₃ | OCH₃ | OCH₃ | OCHF₂ | O | CH | 1.5221 |
| 51 | OCH₃ | CH₃ | ⌬—O— | OCH₃ | OCH₃ | O | CH | 1.5823 |
| 52 | OCH₃ | CH₃ | CH₃—CH—OCHCOOC₂H₅ | OCH₃ | OCH₃ | O | CH | 1.5290 |
| 53 | OCH₃ | C₂H₅ | OCH₃ | OCH₃ | OCH₃ | O | CH | 75-77 |
| 54 | OCH₃ | C₃H₇ | OCH₃ | OCH₃ | OCH₃ | O | CH | 1.5343 |
| 55 | OCH₃ | C₃H₇-i | OCH₃ | OCH₃ | OCH₃ | O | CH | |
| 56 | OCH₃ | ⌬—CH₃ | OCH₃ | OCH₃ | OCH₃ | O | CH | |

TABLE 1-continued (I)

| Compound No. | R | R¹ | R² | A | B | Y | Z | Physical properties: Melting point (°C.) or Refractive index ($n_D^{20}$) |
|---|---|---|---|---|---|---|---|---|
| 57 | $OCH_3$ | $CH_2$-C₆H₅ | $OCH_3$ | $OCH_3$ | $OCH_3$ | O | CH | |
| 58 | $OCH_3$ | $CH_3$ | $OCH_2C*CH$ | $OCH_3$ | $OCH_3$ | O | CH | 77–80.5 |
| 59 | $OCH_3$ | $CH_3$ | cyclohexyl | $OCH_3$ | $OCH_3$ | O | CH | 1.5374 |
| 60 | $OCH_3$ | $CH_3$ | $OC_4H_9$ | $OCH_3$ | $OCH_3$ | O | CH | 1.5772 |
| 61 | $OCH_3$ | $CH_3$ | $OCH_2$-C₆H₄-Cl | $OCH_3$ | $OCH_3$ | O | CH | |
| 62 | $OCH_3$ | $CH_3$ | $OCH_2$-C₆H₄-$OCH_3$ | $OCH_3$ | $OCH_3$ | O | CH | 109–111 |
| 63 | OH | $CH_3$ | $OC_2H_6$ | $OCH_3$ | $OCH_3$ | S | CH | 152–155 |
| 64 | OH | $CH_3$ | $OCH_3$ | $OCH_3$ | $OCH_3$ | S | CH | 144–147 |
| 65 | $OCH_2S$-C₆H₅ | $CH_3$ | $OCH_3$ | $OCH_3$ | $OCH_3$ | O | CH | 1.5687 |

TABLE 1-continued (I)

| Compound No. | R | R¹ | R² | A | B | Y | Z | Physical properties: Melting point (°C.) or Refractive index ($n_D^{20}$) |
|---|---|---|---|---|---|---|---|---|
| 66 | OCH₂SO-phenyl | CH₃ | OCH₃ | OCH₃ | OCH₃ | O | CH | 1.5376 |
| 67 | OCH₂CN | CH₃ | OCH₃ | OCH₃ | OCH₃ | O | CH | 1.5408 |
| 68 | OCH₂OCH₃ | CH₃ | OCH₃ | OCH₃ | OCH₃ | O | CH | 1.5248 |
| 69 | OCH₂OCO—C₄H₉-t | CH₃ | OCH₃ | OCH₃ | OCH₃ | O | CH | 1.5220 |
| 70 | OCH(CH₃)O—COOC₂H₅ | CH₃ | OCH₃ | OCH₃ | OCH₃ | O | CH | |
| 71 | OCH₂OCH₂-phenyl | CH₃ | OCH₃ | OCH₃ | OCH₃ | O | CH | 1.5589 |
| 72 | —OCH₂N(phthalimide) | CH₃ | OCH₃ | OCH₃ | OCH₃ | O | CH | 170-172 |
| 73 | ON=C(CH₃)₂ | CH₃ | OCH₃ | OCH₃ | OCH₃ | O | CH | 1.5355 |
| 74 | ON=C(C₂H₅)₂ | CH₃ | OCH₃ | OCH₃ | OCH₃ | O | CH | 103-105 |
| 75 | OCH₂C≡CH | CH₃ | OCH₃ | OCH₃ | OCH₃ | O | CH | 95-98 |
| 76 | OCH₂CH=CH₂ | CH₃ | OCH₃ | OCH₃ | OCH₃ | O | CH | 1.5465 |
| 77 | OCH₃ | CH₃ | OCH₃ | OCH₃ | N(CH₃)₂ | O | CH | |
| 78 | OCH₃ | CH₃ | OCH₂CCl=CH₂ | OCH₃ | OCH₃ | O | CH | 54-56 |
| 79 | OCH₃ | CH₃ | OCH₂CCl=CHCl | OCH₃ | OCH₃ | O | CH | 1.5468 |
| 80 | OCH₃ | CH₃ | OCH₂CCl=CHCl | OCH₃ | OCH₃ | O | CH | 1.5510 |
| 81 | OCH₃ | CH₃ | OCH₂OC₂H₅ | OCH₃ | OCH₃ | O | CH | 1.5210 |

TABLE 1-continued $$\begin{matrix} R^2-N \\ R^1-C \end{matrix} \diagdown \underset{\underset{COR}{|}}{\bigcirc} -Y-C \diagup \underset{N}{\overset{N}{\diagdown}} \underset{B}{\overset{Z}{\diagup}} \quad (I)$$

| Compound No. | R | R$^1$ | R$^2$ | A | B | Y | Z | Physical properties: Melting point (°C.) or Refractive index ($n_D^{20}$) |
|---|---|---|---|---|---|---|---|---|
| 82 | OCH$_3$ | CH$_3$ | OCH$_2$OCH$_2$— | OCH$_3$ | OCH$_3$ | O | CH | 1.5373 |
| 83 | OCH$_3$ | CH$_3$ | OCOCH$_3$ | OCH$_3$ | OCH$_3$ | O | CH | 1.5510 |
| 84 | OCH$_3$ | CH$_3$ | OCOC$_4$H$_9$-t | OCH$_3$ | OCH$_3$ | O | CH | 1.5291 |
| 85 | OCH$_3$ | CH$_3$ | cyclopropyl-OCO | OCH$_3$ | OCH$_3$ | O | CH | 94–96 |
| 86 | OCH$_3$ | CH$_3$ | phenyl-OCO | OCH$_3$ | OCH$_3$ | O | CH | 121–125 |
| 87 | OCH$_3$ | CH$_3$ | 4-F-phenyl-OCO | OCH$_3$ | OCH$_3$ | O | CH | 1.5377 |
| 88 | OCH$_3$ | CH$_3$ | OCOOCH$_3$ | OCH$_3$ | OCH$_3$ | O | CH | 122–126 |
| 89 | OCH$_3$ | CH$_3$ | phenyl-OCONH | OCH$_3$ | OCH$_3$ | O | CH | 1.5508 |
| 90 | OCH$_3$ | CH$_3$ | OCH$_2$Cl | OCH$_3$ | OCH$_3$ | O | CH | 1.5540 |
| 91 | OCH$_3$ | CH$_3$ | O(CH$_2$)$_2$Cl | OCH$_3$ | OCH$_3$ | O | CH | 1.5539 |
| 92 | OCH$_3$ | CH$_3$ | O(CH$_2$)$_3$Cl | OCH$_3$ | OCH$_3$ | O | CH | 1.5576 |
| 93 | OCH$_3$ | CH$_3$ | OCH$_2$C(Br)=CH$_2$ | OCH$_3$ | OCH$_3$ | O | CH | |

TABLE 1-continued

(I)

| Compound No. | R | R¹ | R² | A | B | Y | Z | Physical properties: Melting point (°C.) or Refractive index ($n_D^{20}$) |
|---|---|---|---|---|---|---|---|---|
| 94 | OCH₃ | CH₃ | OCH₂–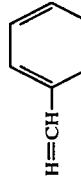 | OCH₃ | OCH₃ | O | CH | 1.5438 |
| 95 | OCH₃ | CH₃ | OCH₂CH=CHCH₃ | OCH₃ | OCH₃ | O | CH | 1.5520 |
| 96 | OCH₃ | CH₃ | OCH₂CH₂=CH₂ | OCH₃ | OCH₃ | O | CH | 1.5473 |
| 97 | OCH₃ | CH₃ | OCOC₂H₆ | OCH₃ | OCH₃ | O | CH | |
| 98 | OCH₃ | CH₃ | OCOC₃H₇ | OCH₃ | OCH₃ | O | CH | |
| 99 | OCH₃ | CH₃ | OCOCH₂Cl | OCH₃ | OCH₃ | O | CH | |
| 100 | OCH₃ | CH₃ | OCOOC₂H₅ | OCH₃ | OCH₃ | O | CH | |
| 101 | OCH₃ | CH₃ | OCON(CH₃)₂ | OCH₃ | OCH₃ | O | CH | 110-111 |
| 102 | OCH₃ | CH₃ | OCOCF₃ | OCH₃ | OCH₃ | O | CH | 1.5496 |
| 103 | OCH₃ | CH₃ | OCH₂C(CH₃)=CH₂ | OCH₃ | OCH₃ | O | CH | |
| 104 | OCH₃ | CH₃ | OCH₂CH=CH– | OCH₃ | OCH₃ | O | CH | 1.5572 |
| 105 | OCH₃ | CH₃ | OCH₂CH=CHCl | OCH₃ | OCH₃ | O | CH | 1.5588 |
| 106 | OCH₃ | CH₃ | OCH₂CH=CCl | OCH₃ | OCH₃ | O | CH | 1.5579 |
| 107 | OCH₃ | CH₃ | OCH₂CF₃ | OCH₃ | OCH₃ | O | CH | |
| 108 | OCH₃ | CH₃ | OC(CH₃)₃ | OCH₃ | OCH₃ | O | CH | 1.5339 |
| 109 | OCH₃ | CH₃ | OSi(CH₃)₃ | OCH₃ | OCH₃ | O | CH | |
| 110 | OCH₃ | CH₃ |  | OCH₃ | OCH₃ | O | CH | |
| 111 | OCH₃ | CH₃ | OCH₂CH=C(CH₃)₂ | OCH₃ | OCH₃ | O | CH | 1.5341 |
| 112 | OCH₃ | CH₃ | OC₄H₉-s | OCH₃ | OCH₃ | O | CH | 1.5407 |
| 113 | OCH₃ | CH₃ |  | OCH₃ | OCH₃ | O | CH | |

TABLE 1-continued (I)
R²—N
R¹—C
  ‖
  N
COR
[structure with Y, Z, A, B substituents]

| Compound No. | R | R¹ | R² | A | B | Y | Z | Physical properties: Melting point (°C.) or Refractive index ($n_D^{20}$) |
|---|---|---|---|---|---|---|---|---|
| 114 | OCH₃ | CH₃ | 4-(OCH₂CH₂CH₂O)-C₆H₄ | OCH₃ | OCH₃ | O | CH | |
| 115 | OCH₃ | CH₃ | 3-(OCH₂CH₂O)-C₆H₄-CH₃ | OCH₃ | OCH₃ | O | CH | |
| 116 | OCH₃ | CH₃ | (OCH₂CH₂O)-C₆H₅ | OCH₃ | OCH₃ | O | CH | 1.5724 |
| 117 | OCH₃ | CH₃ | 4-Cl-C₆H₄-OCH₂CH₂CH₂O- | OCH₃ | OCH₃ | O | CH | |
| 118 | OCH₃ | CH₃ | C₆H₅-CH₃ | OCH₃ | OCH₃ | O | CH | 158-162 |

TABLE 1-continued

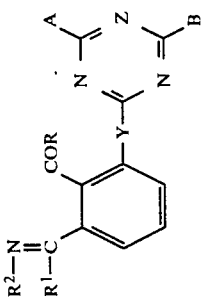

(I)

| Compound No. | R | R[1] | R[2] | A | B | Y | Z | Physical properties: Melting point (°C.) or Refractive index ($n_D^{20}$) |
|---|---|---|---|---|---|---|---|---|
| 119 | OCH₃ | CH₃ | 3-CH₃-C₆H₄ | OCH₃ | OCH₃ | O | CH | 112–115 |
| 120 | OCH₃ | CH₃ | 4-Cl-C₆H₄ | OCH₃ | OCH₃ | O | CH | 169–171 |
| 121 | OCH₃ | CH₃ | 4-OCH₃-C₆H₄ | OCH₃ | OCH₃ | O | CH | 133–135 |
| 122 | OCH₃ | CH₃ | C₃H₇ | OCH₃ | OCH₃ | O | CH | 108–112 |
| 123 | OCH₃ | CH₃ | C₂H₅ | OCH₃ | OCH₃ | O | CH | |
| 124 | OCH₃ | CH₃ | C₃H₇-i | OCH₃ | OCH₃ | O | CH | |
| 125 | OCH₃ | CH₃ | C₄H₉ | OCH₃ | OCH₃ | O | CH | |
| 126 | OCH₃ | CH₃ | C₄H₉-t | OCH₃ | OCH₃ | O | CH | |
| 127 | OCH₃ | CH₃ | C₂H₄OCH₃ | OCH₃ | OCH₃ | O | CH | |
| 128 | OCH₃ | CH₃ | CH₂CH=CH₂ | OCH₃ | OCH₃ | O | CH | |
| 129 | OH | CH₃ | OC₃H₇-i | OCH₃ | OCH₃ | S | CH | 164–168 |
| 130 | OH | CH₃ | OCH₂CH=CH₂ | OCH₃ | OCH₃ | S | CH | 123–125 |
| 131 | OCH₃ | CH₃ | OCH₃ | OCH₃ | OCH₃ | NCHO | CH | 147–149 |
| 132 | OCH₃ | CH₃ | OCH₃ | OCH₃ | OCH₃ | NCOCH₃ | CH | 100–102.5 |
| 133 | OCH₃ | CH₃ | OCH₃ | OCH₃ | OCH₃ | NCOOCH₃ | CH | 95–97 |
| 134 | OCH₃ | H | OCH₃ | OCH₃ | OCH₃ | S | CH | |
| 135 | OCH₃ | H | OC₂H₅ | OCH₃ | OCH₃ | S | CH | |

TABLE 1-continued
(I)
| Compound No. | R | R¹ | R² | A | B | Y | Z | Physical properties: Melting point (°C.) or Refractive index ($n_D^{20}$) |
|---|---|---|---|---|---|---|---|---|
| 136 | OCH₂CO-C₆H₅ | CH₃ | OCH₃ | OCH₃ | OCH₃ | O | CH | 118–121 |
| 137 | imidazolyl | CH₃ | OCH₃ | OCH₃ | OCH₃ | O | CH | 194–199 |
| 138 | SCH₃ | CH₃ | OCH₃ | OCH₃ | OCH₃ | O | CH | |
| 139 | SC₂H₅ | CH₃ | OCH₃ | OCH₃ | OCH₃ | O | CH | |
| 140 | S-C₆H₅ | CH₃ | OCH₃ | OCH₃ | OCH₃ | O | CH | 73–88 |
| 141 | S-C₆H₄-Cl | CH₃ | OCH₃ | OCH₃ | OCH₃ | O | CH | |
| 142 | S-C₆H₄-CH₃ | CH₃ | OCH₃ | OCH₃ | OCH₃ | O | CH | |

TABLE 1-continued (I)

[Structure: R²−N=C(R¹)− and −COR groups on a benzene ring, connected via Y to a triazine ring with substituents A, B, Z, and two N atoms]

| Compound No. | R | R¹ | R² | A | B | Y | Z | Physical properties: Melting point (°C.) or Refractive index ($n_D^{20}$) |
|---|---|---|---|---|---|---|---|---|
| 143 | S—⟨C₆H₄⟩—OCH₃ | CH₃ | OCH₃ | OCH₃ | OCH₃ | O | CH | |
| 144 | SCH₂—⟨C₆H₅⟩ | CH₃ | OCH₃ | OCH₃ | OCH₃ | O | CH | |
| 145 | SCH₂—⟨C₆H₄⟩—Cl | CH₃ | OCH₃ | OCH₃ | OCH₃ | O | CH | |
| 146 | N(CH₃)(CH₃) | CH₃ | OCH₃ | OCH₃ | OCH₃ | O | CH | 1.5491 |
| 147 | N(OCH₃)(CH₃) | CH₃ | OCH₃ | OCH₃ | OCH₃ | O | CH | |
| 148 | N(C₂H₅)(C₂H₅) | CH₃ | OCH₃ | OCH₃ | OCH₃ | O | CH | |
| 149 | NHC₂H₅ | CH₃ | OCH₃ | OCH₃ | OCH₃ | O | CH | |
| 150 | NHC₃H₇ | CH₃ | OCH₃ | OCH₃ | OCH₃ | O | CH | 103–104.5 |

TABLE 1-continued (I)

| Compound No. | R | R¹ | R² | A | B | Y | Z | Physical properties: Melting point (°C.) or Refractive index ($n_D^{20}$) |
|---|---|---|---|---|---|---|---|---|
| 151 | OCH₂CON(CH₃)(CH₃) | CH₃ | OCH₃ | OCH₃ | OCH₃ | O | CH | unmeasurable |
| 152 | OCH₂COCH₃ | CH₃ | OCH₃ | OCH₃ | OCH₃ | O | CH | 1.5329 |
| 153 | OCH₂CO-C₆H₅ | CH₃ | OCH₃ | OCH₃ | OCH₃ | O | CH | 118–121 |
| 154 | OCH₂SCH₃ | CH₃ | OCH₃ | OCH₃ | OCH₃ | O | CH | 1.5459 |
| 155 | OCH₂SO₂-C₆H₅ | CH₃ | OCH₃ | OCH₃ | OCH₃ | O | CH | unmeasurable |
| 156 | OCH₂NO₂ | CH₃ | OCH₃ | OCH₃ | OCH₃ | O | CH | |
| 157 | O(CH₂)₂Cl | CH₃ | OCH₃ | OCH₃ | OCH₃ | O | CH | |
| 158 | OCH₂CF₃ | CH₃ | OCH₃ | OCH₃ | OCH₃ | O | CH | |
| 159 | OCH₂-C₆H₄-OCH₃ | CH₃ | OCH₃ | OCH₃ | OCH₃ | O | CH | |
| 160 | OCH₃ | CH₃ | OCH₃ | N(CH₃)₂ | OCH₃ | O | N | 1.5378 |
| 161 | OCH₃ | CH₂Cl | OCH₃ | OCH₃ | OCH₃ | O | CH | |
| 162 | OCH₃ | CH₂Br | OCH₃ | OCH₃ | OCH₃ | O | CH | |
| 163 | OCH₃ | CH₂OCH₃ | OCH₃ | OCH₃ | OCH₃ | O | CH | |
| 164 | OCH₃ | CH₂OC₂H₅ | OCH₃ | OCH₃ | OCH₃ | O | CH | |
| 165 | OCH₃ | CH₂SCH₃ | OCH₃ | OCH₃ | OCH₃ | O | CH | |
| 166 | OCH₃ | CH₂SC₂H₅ | OCH₃ | OCH₃ | OCH₃ | O | CH | 1.5210 |

TABLE 1-continued

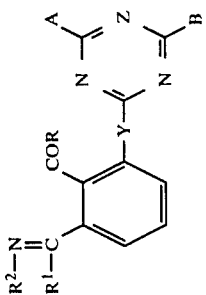
(I)

| Compound No. | R | R$^1$ | R$^2$ | A | B | Y | Z | Physical properties: Melting point (°C.) or Refractive index ($n_D^{20}$) |
|---|---|---|---|---|---|---|---|---|
| 167 | OCH$_3$ | CH$_2$CN | OCH$_3$ | OCH$_3$ | OCH$_3$ | O | CH | |
| 168 | OCH$_3$ | CH$_3$ | OCH$_2$—CH$_2$N(CH$_3$)CH$_3$ | OCH$_3$ | OCH$_3$ | O | CH | |
| 169 | OCH$_2$—CH$_2$N(CH$_3$)CH$_3$ | CH$_3$ | OCH$_3$ | OCH$_3$ | OCH$_3$ | O | CH | |
| 170 | cyclohexanone oxime (ON=) | CH$_3$ | OCH$_3$ | OCH$_3$ | OCH$_3$ | O | CH | |
| 171 | OCH$_2$—C(Cl)=CH$_2$ | CH$_3$ | OCH$_3$ | OCH$_3$ | OCH$_3$ | O | CH | |
| 172 | OCH$_2$C•C—CH$_2$Cl | CH$_3$ | OCH$_3$ | OCH$_3$ | OCH$_3$ | O | CH | |
| 173 | OCH$_3$ | CH$_2$SCH$_3$→O | OCH$_3$ | OCH$_3$ | OCH$_3$ | O | CH | |
| 174 | OCH$_3$ | O←CH$_2$SCH$_3$→O | OCH$_3$ | | | | | |

TABLE 1-continued $$\text{(I)}$$

Structure:

$R^2-N=C(R^1)-$ attached to a benzene ring bearing a COR group, with the ring also bonded via Y to a triazine/pyrimidine ring having substituents A, B and Z=N or CH.

| Compound No. | R | $R^1$ | $R^2$ | A | B | Y | Z | Physical properties: Melting point (°C.) or Refractive index ($n_D^{20}$) |
|---|---|---|---|---|---|---|---|---|
| 175 | OCH₃ | CH₂CCH₃‖O | OCH₃ | OCH₃ | OCH₃ | O | CH | |
| 176 | OCH₃ | CH₃ | ‖O‖OCH₃C (phenyl) | OCH₃ | OCH₃ | O | CH | |
| 177 | OCH₃ | CH₃ | ‖O‖OCH₂CCH₃ | OCH₃ | OCH₃ | O | CH | |
| 178 | OCH₃ | CH₃ | OCH₂C*C—CH₂Cl | OCH₃ | OCH₃ | O | CH | |
| 179 | OCH₃ | CH₃ | OCH₃ | OCH₃ | OCH₃ | O | CH | |
| 180 | O-phenyl | CH₃ | OCH₃ | OCH₃ | OCH₃ | O | CH | |
| 181 | O-(4-Cl-phenyl) | CH₃ | OCH₃ | CF₃ | OCH₃ | O | CH | |
| 182 | OCH₂CNH₂‖O | CH₃ | OCH₃ | OCH₃ | OCH₃ | O | CH | 121–125 |

TABLE 1-continued (I)

[Structural formula showing a benzene ring with substituents: R²−N=C(R¹)− group, −COR group, and −Y−C(=N−)(−N=) linked to A and B groups with Z]

| Compound No. | R | R¹ | R² | A | B | Y | Z | Physical properties: Melting point (°C.) or Refractive index ($n_D^{20}$) |
|---|---|---|---|---|---|---|---|---|
| 183 | OCH₃ | CH₃ | CH(CH₃)OC₆H₅ | OCH₃ | OCH₃ | O | CH | 1.5402 |

Note:
Compound No. 9 and Compound No. 10 are structural isomers each other.
Compound No. 46 and Compound No. 47 are structural isomers each other.
• ≡ Triple bond
Compound No. 79 and Compound No. 80 are structural isomers each other.

The compound of the present invention can be prepared, for example, by the following Processes A to F.

PROCESS A

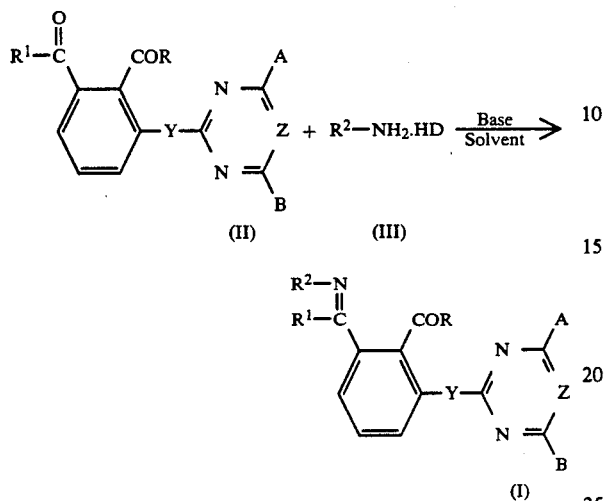

(wherein R, $R^1$, $R^2$, A, B, Z and Y are as defined above, and HD represents an acid for forming a salt with an amine, for example a corresponding acid for forming sulfate, hydrochloride or the like.)

The compound of the general formula [I] of the present invention can be prepared by reacting the compound of the general formula [II] with the compound of the general formula [III] in the presence of a base in an inert solvent at a temperature in the range from 0° C. to the boiling point of the solvent for 30 minutes to 12 hours. As the base, a carbonate, hydrogencarbonate, acetate, alcholate, hydroxide, hydride or oxide of an alkali metal such as sodium and potassium or of an alkaline earth metal such as magnesium and calcium, may be employed. In addition, an organic base, for example, pyridine or tertiary amine such as triethylamine, may be employed.

As the solvent, a hydrocarbon solvent such as toluene, benzene, xylene or the like, a halogenated hydrocarbon solvent such as methylene chloride, chloroform or the like, an alcohol solvent such as methanol, ethanol or the like, an ether solvent such as ethyl ether, isopropyl ether, tetrahydrofuran, 1,4-dioxane or the like, an aprotic polar solvent such as N,N-dimethylformamide, N,N-dimethylacetamide, dimethylsulfoxide or the like, and an ester solvent such as ethyl acetate or the like, may be employed Preferable combination examples of a solvent and a base include the combination of methanol and potassium acetate and the combination of chloroform and triethylamine.

PROCESS B

The compound of the general formula [I] of the present invention may also be prepared by reacting the compound of the general formula [II] with an amine of the general formula [IV], such as hydrazines, anilines, hydroxyamines or the like, preferably in a solvent, as shown in the following reaction formula:

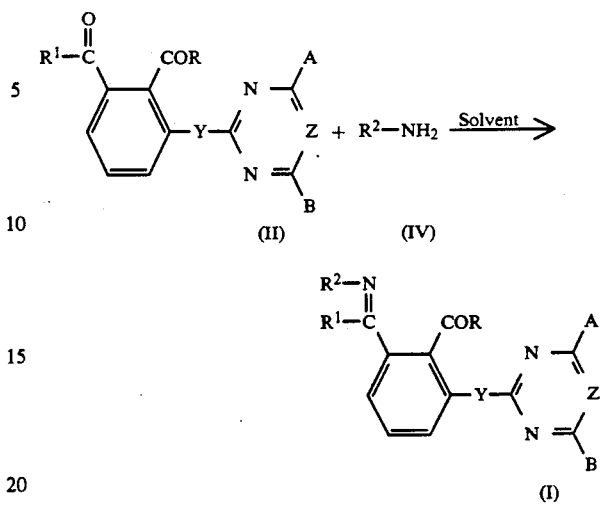

(wherein R, $R^1$, $R^2$, A, B, Y and Z are as defined above).

The solvent and the reaction temperature used in this process may be the same as those employed in the above-mentioned Process A. One of the preferable reaction conditions includes a refluxing in methanol solvent.

The compounds of the general formula [II] used as a starting material in the above Processes A and B is also a novel compound, and can be prepared as illustrated in the following reaction formulas.

(a) The compound of the general formula [II] wherein Y is an oxygen atom or a sulfur atom:

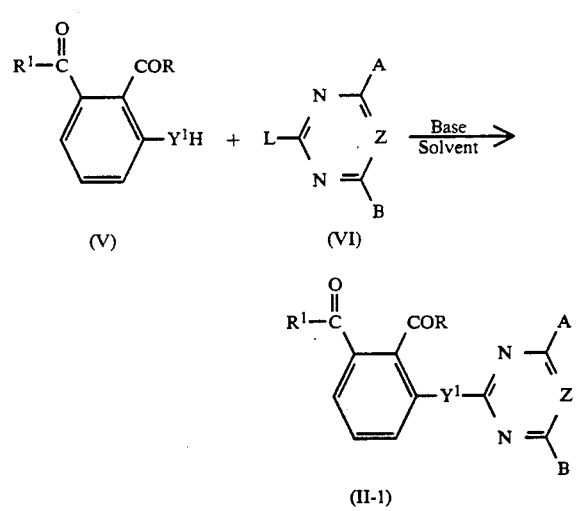

(wherein $Y^1$ is an oxygen atom or a sulfur atom, and R, $R^1$, A, B and Z are as defined above, L representing an eliminating group).

That is, the compound of the general formula [II-1] can be prepared by reacting the compound of the general formula [V] with the compound of the general formula [VI] in the presence of a base in an inert solvent at a temperature in the range from 0° C. to the boiling point of the solvent. The base and the solvent used in this process may be the same as those described above. Preferable combination examples of the solvent and the base include the combination of dimethylformamide and potassium carbonate or the combination of dimethylformamide and sodium hydride.

The compound of the general formula [V] is well known, and can be prepared, for example, in accordance with the process described in the Pharmaceutical Journal, Vol. 74, p.466 (1954).

The compound of the general formula [V] may also be prepared in accordance with the following two synthesis routes as illustrated by the following reaction formulas

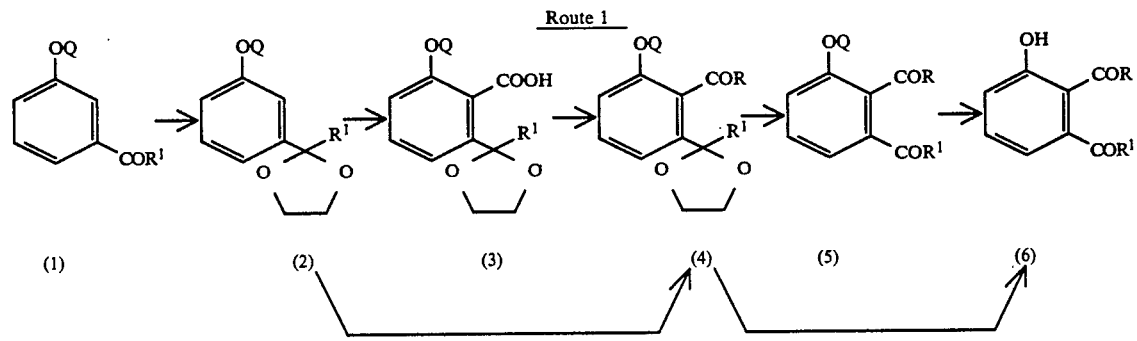

(wherein Q represents an alkyl group, an alkoxyalkyl group or a benzyl group, and R and $R^1$ are as defined above).

The acylphenone derivative of the general formula (1) is acetalized with ethylene glycol in the presence of a Lewis acid to obtain the compound of the general formula (2). The compound of the general formula (2) is then reacted with carbon dioxide in the presence of an organic metal such as n-butyl lithium or phenyl lithium in a inert solvent such as n-hexane, toluene or benzene to obtain the compound of the general formula (3). The resultant compound is then esterified by normal method, and the protecting groups of acetal and hydroxyl groups are then eliminated in order or simultaneously to obtain the aimed product. The compound of the general formula (4) may also be prepared by reacting the compound of the general formula (2) with a halo-formic acid ester in the presence of an organic metal such as n-butyl lithium or phenyl lithium in an inert solvent such as n-hexane, toluene or benzene.

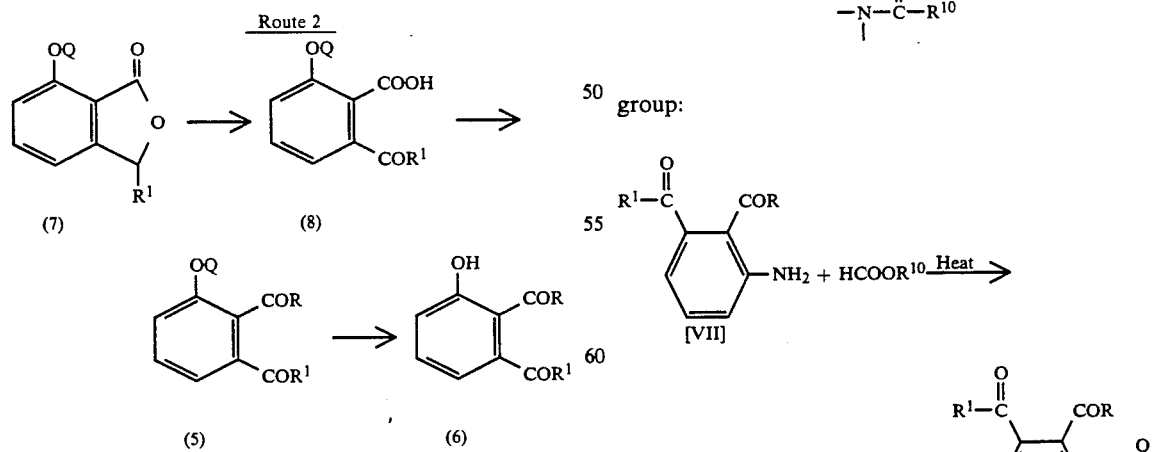

(wherein R, $R^1$ and Q are as defined above).

The phthalide derivative of the general formula (7) is hydrolyzed under oxidation condition in the presence of potassium permanganate and magnesium nitrate to obtain the salicylic acid derivative of the general formula (8).

The resultant compound is then esterified by normal method, and the protecting group of a hydroxyl group is selectively eliminated to obtain the aimed compound.

The compound of the general formula [V] wherein $Y^1$ is a sulfur atom can be prepared from the compound of the general formula [VII] disclosed in the above reference as illustrated in the following reaction formula:

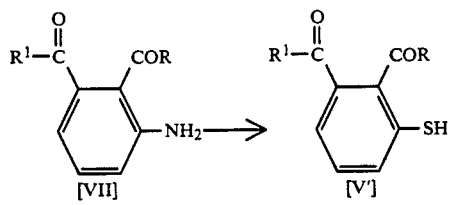

(wherein R and $R^1$ are as defined above).

(b) The compound of the general formula [II] wherein Y represents an —NH— group or an $$-\underset{|}{N}-\overset{O}{\underset{\|}{C}}-R^{10}$$

group:

-continued

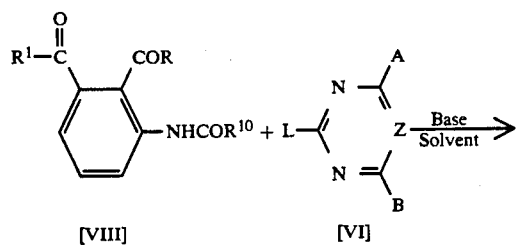

[VIII] [VI]

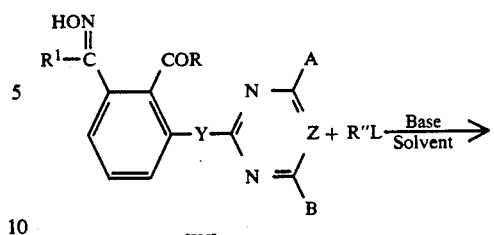

[IX]

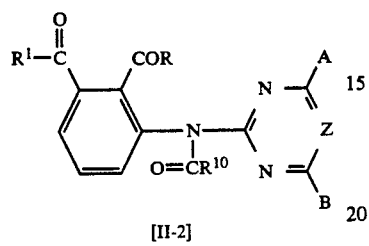

[II-2]

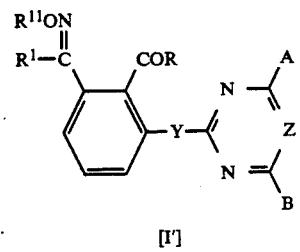

[I']

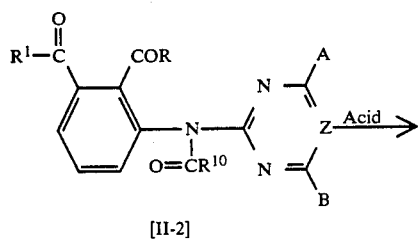

[II-2]

(wherein R, R¹, A, B, Y and Z are as defined above, and R¹¹ represents an alkyl group, a phenyl group, an alkenyl group, an alkynyl group, a benzyl group, an alkoxycarbonylalkyl group or a cycloalkyl group, L representing an eliminating group).

The compound of the formula [IX] can be prepared, for example, by reacting the compound of the general formula [II] with the hydroxyamine salt of the general formula [X] in the same manner as in the above Process A.

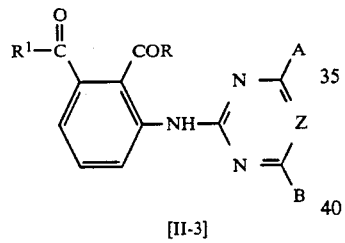

[II-3]

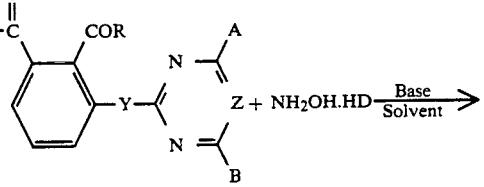

[II]    [X]

(wherein R, R¹, A, B, Z and L are as defined above).

That is, the amino group of the anthranylic acid derivative of the general formula [VII] disclosed in the above reference is formylated with formic acid to obtain the compound of the general formula [VIII]. The resultant compound is reacted with the pyrimidine or triazine derivative of the general formula of [VI] to obtain the anthranylic acid derivative of the general formula [II-2]. In this case, the reaction conditions including solvent, base, reaction temperature and reaction time used in this process are the same as those used in Process A. The resultant compound may further be deformylated to obtain the compound of the general formula [II-3].

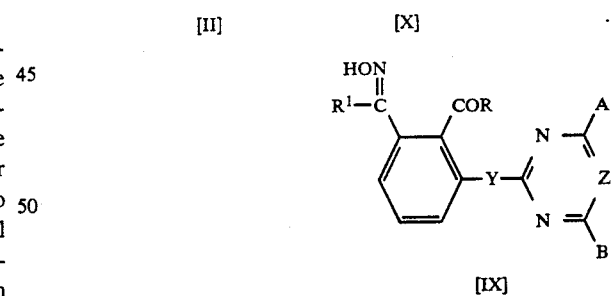

[IX]

(wherein R, R¹, A, B, Z, Y and HD are as defined above).

PROCESS C

The compound of the present invention may also be prepared by alkylating the corresponding oxime with an alkylating agent as illustrated in the following reaction formula. Examples of the alkylating agent include alkyl halide, alkenyl halide, benzyl halide, halogen-substituted aliphatic acid ester, cycloalkyl halide, alkyl sulfate or the like.

PROCESS D

The compound of the present invention may also be prepared by reacting the compound of the general formula [XI] with the compound of the general formula [VI] in the presence of a base in an inert solvent at a temperature in the range from 0° C. to the boiling point of the solvent. The base and the solvent used in this process may be the same as those used in the synthesis of the material of the general formula [II] in accordance with Process A.

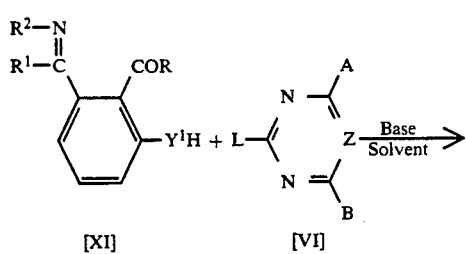

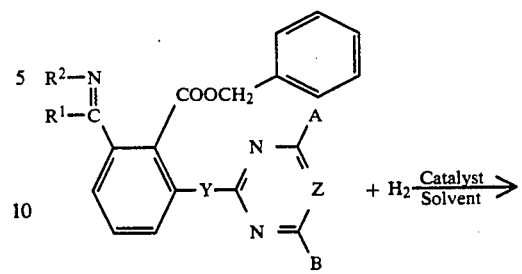

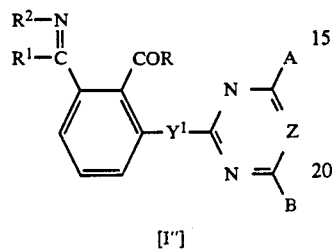

[I″]

(wherein R, R¹, A, B, Y¹, Z and L are as defined above).

The compound of the general formula [XI] which is the starting material of the above reaction is also a novel compound, and can be prepared, for example, by reacting the compound of the formula [V] disclosed in the above reference with the amine salt of the formula [III] in the same manner as in Process A in accordance with the following reaction formula:

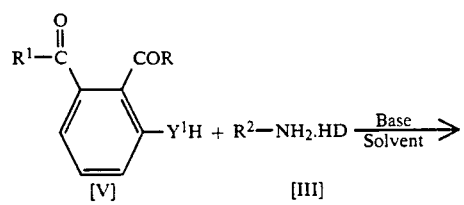

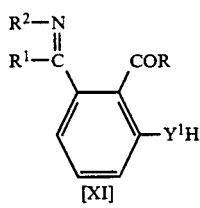

(wherein R, R¹, R², Y and HD are as defined above).

PROCESS E

The compound of the present invention having the general formula [I] wherein R is hydroxy group can be obtained by catalytically hydrogen-reducing the compound of the general formula [I] wherein R is a benzyloxy group, in the presence of a catalyst such as Raney nickel, palladium carbon or the like.

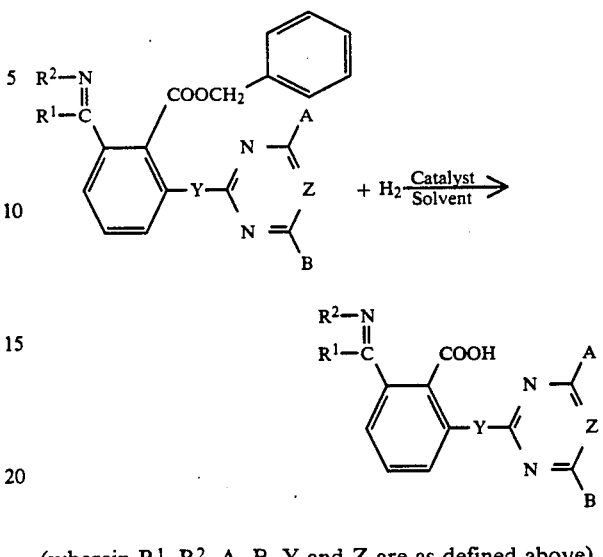

(wherein R¹, R², A, B, Y and Z are as defined above).

PROCESS F

The compound of the present invention may also be prepared as illustrated in the following reaction formula:

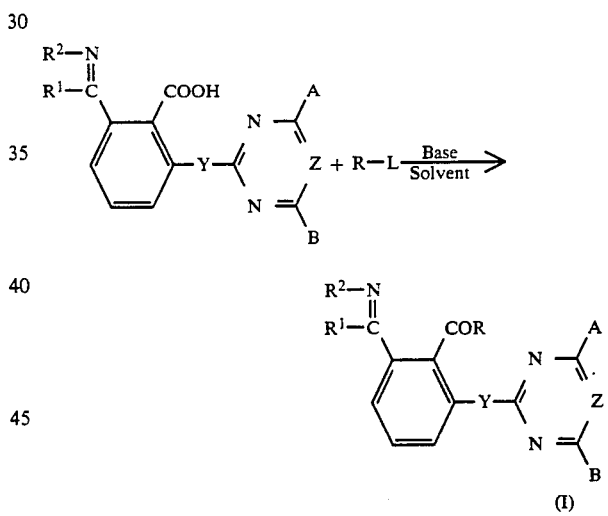

(wherein R, R¹, R², A, B, Z, Y and L are as defined above).

For example, the compound of the present invention can also be prepared by condensing a benzoic acid derivative obtained by Process E with an ester residue having a corresponding eliminating group in the presence of a suitable base such as potassium carbonate, sodium hydride or the like in a suitable inert solvent such as dimethylformamide, tetrahydrofuran, acetonitrile, toluene or the like, at a temperature in the range from room temperature to 100° C.

Typical examples of intermediate products having the general formula [II] or [XI] for the compounds of the present invention are listed in the following Tables 2-1 and 2-2.

These intermediate products also have excellent herbicidal activities and selectivities.

TABLE 2-1

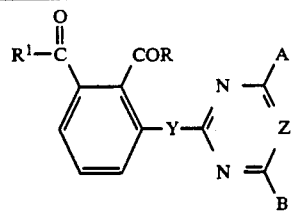
(II)

| Intermediate compound No. | R | R¹ | A | B | Y | Z | Physical properties: Melting point (°C.) or Refractive index ($n_D^{20}$) |
|---|---|---|---|---|---|---|---|
| 1 | OH | $CH_3$ | $OCH_3$ | $OCH_3$ | O | CH | 163–165 |
| 2 | $OCH_2C_6H_5$ | $CH_3$ | $OCH_3$ | $OCH_3$ | O | CH | 141–143 |
| 3 | $OCH_3$ | $CH_3$ | $OCH_3$ | $OCH_3$ | O | CH | 164–166 |
| 4 | $OC_2H_5$ | $CH_3$ | $OCH_3$ | $OCH_3$ | O | CH | |
| 5 | $OC_3H_7$ | $CH_3$ | $OCH_3$ | $OCH_3$ | O | CH | 84.5–86 |
| 6 | $OC_3H_7$-i | $CH_3$ | $OCH_3$ | $OCH_3$ | O | CH | |
| 7 | $OCH_3$ | $CH_3$ | $OCH_3$ | $OCH_3$ | S | CH | 149–151 |
| 8 | $OCH_3$ | $CH_3$ | Cl | $OCH_3$ | O | CH | 117.5–120 |
| 9 | $OCH_3$ | $CH_3$ | Cl | $CH_3$ | O | CH | 109–112 |
| 10 | $OCH_3$ | $CH_3$ | $CH_3$ | $OCH_3$ | O | CH | 127–130 |
| 11 | $OCH_3$ | $CH_3$ | $OC_2H_5$ | $OC_2H_5$ | O | CH | 117–118.5 |
| 12 | $OCH_3$ | $CH_3$ | $CH_3$ | $CH_3$ | O | CH | 138–140 |
| 13 | $OCH_3$ | $CH_3$ | $OCH_3$ | $OCH_3$ | O | N | 151–156 |
| 14 | $OCH_3$ | $CH_3$ | $OCH_3$ | $OCH_3$ | NH | CH | 108–110 |
| 15 | $OCH_3$ | $CH_3$ | $OCHF_2$ | $OCH_3$ | O | CH | 70–73 |
| 16 | OH | $CH_3$ | $OCH_3$ | $OCH_3$ | S | CH | 177–180 |
| 17 | $OCH_3$ | $C_2H_5$ | $OCH_3$ | $OCH_3$ | O | CH | 120–122 |
| 18 | $OCH_3$ | H | $OCH_3$ | $OCH_3$ | O | CH | 91–93 |
| 19 | $OCH_3$ | $CH_3$ | $N(CH_3)_2$ | $OCH_3$ | O | N | 145–149 |
| 20 | $OCH_3$ | $CH_3$ | $N(CH_3)_2$ | $OCH_3$ | O | CH | |

TABLE 2-2

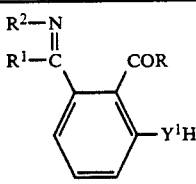
(XI)

| Intermediate compound No. | R | R¹ | R² | Y¹ | Physical properties: Melting point (°C.) or Refractive index ($n_D^{20}$) |
|---|---|---|---|---|---|
| 21 | $OCH_3$ | $CH_3$ | $OCH_3$ | O | 1.5423 |
| 22 | OH | $CH_3$ | $OCH_3$ | O | 79–81 |
| 23 | $OCH_3$ | $CH_3$ | $OC_6H_5$ | O | |

TABLE 2-2-continued

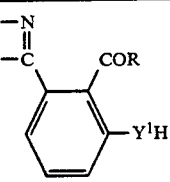
(XI)

| Intermediate compound No. | R | R¹ | R² | Y¹ | Physical properties: Melting point (°C.) or Refractive index ($n_D^{20}$) |
|---|---|---|---|---|---|
| 24 | $OCH_3$ | $CH_3$ | $OCH_2C_6H_5$ | O | |
| 25 | $OCH_3$ | $C_2H_5$ | $OCH_3$ | O | |

EXAMPLE 1

Preparation of methyl 2-[(4,6-dimethoxypyrimidin-2-yl)oxy]-6-[1-(N-methoxyimino)ethyl]benzoate (Compound No. 9)

5 g of methyl 2-acetyl-6-[(4,6-dimethoxypyrimidin-2-yl)oxy]benzoate (melting point=164° to 166° C.), 3 g of methanolamine hydrochloride and 3.6 g of triethylamine were added to 50 ml of chloroform, and the mixture was reacted with stirring for 8 hours under refluxing. The reaction liquor was poured into a large amount of water, and the chloroform layer was separated out after washing with water, the solvent being then distilled off under reduced pressure after drying. An oily product was purified by column chromatography using hexane/isopropyl ether as a developing solvent, and was recrystallized in a hexane/isopropyl ether mixture solvent to obtain 3.2 g of the aimed compound of a colorless transparent prism-like crystal (melting point=105 to 106° C.) at a yield of 50%.

EXAMPLE 2

Preparation of methyl 2-[(4,6-dimethoxypyrimidin-2-yl)oxy]-6-[1-[N-methoxyimino)ethyl]benzoate (Compound No. 9)

3.3 g of methyl 2-acetyl-6-[(4,6-dimethoxypyrimidin-2-yl)oxy]benzoate, 4.1 g of methanolamine hydrochloride and 4.9 g of potassium acetate were added to 50 ml of methanol, and the mixture was reacted with stirring for 2 hours under refluxing by heating. The reaction liquor was poured into a large amount of water, and the product was extracted with ethyl acetate after being made acidic with hydrochloric acid, the product being washed with sodium hydrogencarbonate aqueous solution and water in sequence. After drying, the concentrated crystal thus obtained was washed with isopropyl ether to obtain 3.2 g of the aimed product (melting point=105° to 106° C.) at a yield of 89%.

REFERENCE EXAMPLE 1

Preparation of methyl 2-[(4,6-dimethoxypyrimidin-2-yl)thio]-6-acetylbenzoate (Intermediate product No. 7)

10.2 g of 2-amino-6-acetylbenzoic acid was converted into a diazonium salt with a mixture of 14.2 ml of concentrated hydrochloric acid, 40 ml of water and 4.3 g of sodium nitrite, and the diazonium salt was gradually added dropwise at a temperature of 0 to 5° C. to a sodium disulfide aqueous solution (prepared from 14.3 g of sodium sulfide.9H$_2$O, 1.9 g of sulfur, 4.6 g of sodium hydroxide and 30 ml of water). After adding dropwise, the reaction liquor was stirred for 2 hours at room temperature to complete the reaction. The reaction liquor was poured into a large amount of water, and after adding concentrated hydrochloric acid thereto, the product was extracted with ethyl acetate. To the ethyl acetate layer, was added sodium hydrogencarbonate aqueous solution, and the content soluble in sodium hydrogencarbonate was extracted. To the resultant aqueous solution, was added 14.8 g of sodium pyrosulfate, and the mixture was refluxed for 30 minutes to complete the reaction. To the reaction liquor, was added concentrated hydrochloric acid, and the product was extracted with ethyl acetate. The extracted liquor was dried, and the solvent was distilled off under reduced pressure to obtain 10.1 g of 2-mercapto-6-acetylbenzoic acid at a yield of 90%.

10.1 g of 2-mercapto-6-acetylbenzoic acid thus obtained and 7.6 g of potassium hydroxide were then dissolved in a mixed solvent of 20 ml of water and 30 ml of N,N-dimethylformamide. To the resultant solution, was added 13.5 g of 4,6-dimethoxy-2-methylsulfonylpyrimidine, and the resultant solution was reacted with stirring at room temperature for 2 hours and further at 60° C. for 0.5 hour. The reaction liquor was then poured into a large amount of water, and the neutral content was extracted with chloroform. Concentrated hydrochloric acid was added to the water layer, and an oily product thus precipitated was extracted with ether and then dried. The ether solution was then passed through a short column of Florisil, and ether was distilled off to obtain 6.1 g of 2-[(4,6-dimethoxypyrimidin-2-yl)thio]-6-acetylbenzoic acid.

After suspending 0.3 g of 60% sodium hydride in 40 ml of a 1:1 mixed solvent of tetrahydrofuran and N,N-dimethylformamide, 2.5 g of the above obtained 2-[(4,6-dimethoxypyrimidin-2-yl)thio]-6-acetylbenzoic acid was added to the suspension, and was stirred for 30 minutes. 1.3 g of methyl iodide was added dropwise to the resultant liquor at room temperature, and the resultant liquor was refluxed by heating for 2 hours to complete the reaction. The reaction liquor was then poured into water, and was extracted with ethyl acetate. The extracted liquor was washed with water and dried to distill off the solvent under reduced pressure. The residue thus obtained was purified by chromatography to obtain 5.8 g of the aimed compound (melting point=149° to 151° C.) at a yield of 32%.

EXAMPLE 3

Preparation of methyl 2-[(4,6-dimethoxypyrimidin-2-yl)thio]-6-[1-(N-methoxyimino)ethyl]benzoate (Compound No. 33)

1.0 g of methyl 2-[(4,6-dimethoxypyrimidin-2-yl)thio]-6-acetylbenzoate and 0.5 g of methoxyamine hydrochloride were dissolved in 6 ml of methanol, and the resultant solution was refluxed for 15 minutes. After cooling the mixed liquor to room temperature, 0.8 g of potassium carbonate was added to this liquor and the resultant liquor was heat-refluxed for 3 hours. The reaction liquor was poured into a large amount of water, and an oily product thus precipitated was extracted with ethyl acetate. The ethyl acetate layer was washed with water, and was dried to distill off ethyl acetate under reduced pressure. The residue thus obtained was purified by chromatography to obtain 0.65 g of the aimed compound (refractive index=1.5709) at a yield of 59%.

EXAMPLE 4

Preparation of methyl 2-[(4,6-dimethoxypyrimidin-2-yl)oxy]-6-(N'-acetylhydrazomethyl)benzoate (Compound No. 27)

0.7 g of methyl 2-[(4,6-dimethoxypyrimidin-2-yl)oxy]-6-formylbenzoate, 0.7 g of acetyl hydrazine and 10 ml of methanol were placed in a 50 ml eggplant type flask, and were stirred for 30 minutes at room temperature. Methanol was distilled off under reduced pressure, and the residue was dissolved in ethyl acetate. The organic layer was washed with water, 5% hydrochloric acid and a saturated salt aqueous solution, and was dried with magnesium sulfate anhydride. After filtering, a small amount of Florisil was added to the resultant product, and was stirred for 5 minutes. The Florisil was filtered out, and ethyl acetate was distilled off under reduced pressure. The solid product thus obtained was washed with isopropyl ether to obtain 0.7 g of the aimed compound (melting point=144° to 146° C.) at a yield of 5%.

REFERENCE EXAMPLE 2

Preparation of methyl 2-[(4,6-dimethoxypyrimidin-2-yl)oxy]-6-formylbenzoate (Intermediate product No. 18)

13.8 g of potassium carbonate and 50 ml of DMF were placed in a 200 ml eggplant type flask, and 11.1 g of methyl 2-formyl-6-hydroxybenzoate and 14.6 g of 4,6-dimethoxy-2-methanesulfonylpyrimidine were added thereto with stirring. The mixture was stirred at 80° C. for 1 hour, and the resultant liquor was poured into an ice water after cooling. An oily product thus precipitated was extracted with ethyl acetate, and was dried with magnesium sulfate anhydride. Ethyl acetate was distilled off under reduced pressure, and the residue thus obtained was purified by column chromatography to obtain 11.0 g of the aimed compound (melting point=91° to 93° C.) at a yield of 52%.

EXAMPLE 5

Preparation of methyl 2-[(4,6-dimethoxypyrimidin-2-yl)oxy]-6-(N'-phenylhydrazomethyl)benzoate (Compound No. 24)

0.9 g of methyl 2-[(4,6-dimethoxypyrimidin-2-yl)oxy]-6-formylbenzoate, 0.7 g of phenylhydrazine hydrochloride, 0.4 g of potassium acetate and 10 ml of methanol were placed in a 50 ml eggplant type flask, and were stirred for 10 minutes at room temperature. Methanol was distilled off under reduced pressure, and the residue was dissolved in ethyl acetate. The organic layer was washed with water, 5% hydrochloric acid and a saturated salt aqueous solution, and was dried with magnesium sulfate anhydride. After filtering, a small amount of Florisil was added to the resultant product, and the resultant product was stirred for 5 minutes. The Florisil was filtered out, and ethyl sulfate was distilled off under reduced pressure to obtain 0.9 g of the aimed compound (physical properties unmeasurable) as a yield of 78%.

EXAMPLE 6

Preparation of methyl 2-[(4,6-dimethoxypyrimidin-2-yl)oxy]-6-(hydroxyiminomethyl)benzoate (Compound No. 19)

2.0 g of methyl 2-[(4,6-dimethoxypyrimidin-2-yl)oxy]-6-formylbenzoate, 0.8 g of hydroxyamine hydrochloride, 1.1 g of potassium acetate and 10 ml of methanol were placed in a 50 ml eggplant type flask, and were stirred for 10 minutes at room temperature. Methanol was distilled off under reduced pressure, and the residue was dissolved in ethyl acetate. The organic layer was washed with water, 5% hydrochloric acid and a saturated salt aqueous solution, and was dried with magnesium sulfate anhydride. After filtering, a small amount of Florisil was added to the resultant product, and was stirred for 5 minutes. The Florisil was filtered out, and ethyl acetate was distilled off under reduced pressure to obtain 1.5 g of the aimed compound (refractive index=1.5558) at a yield of 72%.

EXAMPLE 7

Preparation of methyl 2-[(4,6-dimethoxypyrimidin-2-yl)oxy]-6-[(1-ethoxycarbonylethyl)oxyiminomethyl)benzoate (Compound No. 22)

2 0 g of methyl 2-[(4,6-dimethoxypyrimidin-2-yl)oxy]-6-hydroxyiminomethylbenzoate, 3 ml of ethyl 2-bromopropionate and 0.9 g of silver oxide (I) were place in a 50 ml eggplant type flask, and were allowed to stand for one night at room temperature. 10 ml of acetone and 10 g of silica gel were added to the resultant reaction liquor, and the acetone was distilled off under reduced pressure. The resultant product was purified by column chromatography to obtain 0.7 g of the aimed compound (refractive index=1.5261) at a yield of 27%.

REFERENCE EXAMPLE 3

Preparation of methyl 6-[1-(N-methoxyimino)ethyl]salicylate (Intermediate product No. 21)

1.2 g of methyl 6-acetyl salicylate, 1.3 g of methoxyamine hydrochloride and 1.5 g of potassium acetate were added to 30 ml of methanol, and were stirred for one night at room temperature. After completing the reaction, the reaction liquor was poured into water, and was made acetic with hydrochloric acid to extract the reaction product with ethyl acetate. The reaction product was washed with sodium hydrogencarbonate aqueous solution and water in sequence, and was dried to obtain a concentrated oily product. The product was then purified by column chromatography to obtain 1.15 g of the aimed compound (refractive index=1.5423) at a yield of 83%.

EXAMPLE 8

Preparation of methyl 2-[(4,6-dimethoxypyrimidin-2-yl)oxy]-6-[1-(N-methoxyimino)ethyl]benzoate (Compound No. 9)

1.15 g of methyl 6-[1-(N-methoxyimino)ethyl]salicylate, 1.12 g of 4,6-dimethoxy-2-methylsulfonylpyrimidine and 0.71 g of potassium carbonate were added to 50 ml of DMF, and were heated at 100° C. for 2 hours. After allowing to cool, the reaction liquor was poured into water, and was extracted with ethyl acetate. After washing the extracted product with water, the resultant product was dried and concentrated to obtain a crude crystal of methyl 2-[(4,6-dimethoxypyrimidin-2-yl)oxy]-6-[1-(N-methoxyimino)ethyl benzoate. This product was then washed with diisopropyl ether to obtain 1.35 g of the aimed compound (melting point=105 to 106° C.) at a yield of 73%.

REFERENCE EXAMPLE 4

Preparation of methyl 2-acetyl-6-[(4,6-dimethoxytriazin-2-yl)oxy]benzoate (Intermediate product No. 13)

1.0 g of methyl 6-acetylsalicylate was added to a suspension solution of 0.23 g of sodium hydride and 30 ml of benzene, and the resultant mixture was stirred for 10 minutes at room temperature. 0.95 g of 2-chloro-4,6-dimethoxytriazine was added to the resultant mixture, and the mixture was stirred for one day and one night at room temperature. After completing the reaction, the reaction liquor was poured into water, and was extracted with ethyl acetate. The extracted product was washed with water, dried and concentrated to obtain a crystal. The product thus obtained was purified by column chromatography to obtain 1.15 g of the aimed compound (melting point=151° to 156° C.) at a yield of 67%.

EXAMPLE 9

Preparation of methyl 2-[(4,6-dimethoxytriazin-2-yl)oxy]-6-[1-(N-methoxyimino)ethyl]benzoate (Compound No. 41)

0.9 of methyl 2-acetyl-6-[(4,6-dimethoxytriazin-2-yl)oxy]benzoate, 0.68 g of methoxyamine hydrochloride and 0.80 g of potassium acetate were added to 30 ml of methanol, and the resultant mixture was stirred for one day and one night at room temperature. The resultant reaction liquor was poured into water, and was extracted with ethyl acetate. After washing the extracted product with water, the washed product was dried and concentrated to obtain an oily product. This was then purified by column chromatography to obtain 0.47 g of the aimed compound (melting point=131° to 135° C.) at a yield of 48%.

EXAMPLE 10

Preparation of 2-[(4,6-dimethoxypyrimidin-2-yl)oxy]-6-[1-(N-methoxyimino)ethyl]benzoate (Compound No. 1)

1.5 g of benzyl ester of 2-[(4,6-dimethoxypyrimidin-2-yl)oxy]-6-[(1-(N-methoxyimino)ethyl]benzoic acid (Compound No. 4) prepared in the same manner as in Example 1 and 0.15 g of 10% palladium carbon were added to 50 ml of methanol, and 83 ml of hydrogen was added to the resultant mixture with stirring at room temperature. After completing the reaction, palladium carbon was filtered out, and the solvent was distilled off under reduced pressure. An oily product thus obtained was purified by column chromatography using hexane/ethyl acetate as a developing solvent to obtain 1.1 g of the aimed compound (melting point=125° to 127° C.) at a yield of 86%.

EXAMPLE 11

Preparation of ethyl 2-[(4,6-dimethoxy-2-yl)oxy]-6-[1-(N-methoxyimino)ethyl]benzoate (Compound No. 15)

2 g of methyl 2-[(4,6-dimethoxypyrimidin-2-yl)oxy]-6-[1-(N methoxyimino)ethyl]benzoate obtained in Example 8 was added to 50 ml of DMF, and was fully stirred at room temperature. 0.23 g of sodium hydride was added to the resultant liquor, and 1 g of ethyl bromide was added thereto after the generation of hydrogen stopped. The resultant mixture was stirred for one hour at 60° C. The reaction liquor was then poured into a cold water, and an oily product thus formed was extracted with ethyl acetate. The extracted oily product was washed with water, dried and concentrated. The residue oily product was purified by column chromatography using hexane/isopropyl ether (10:1) as a developing solvent to obtain 1.5 g of the aimed compound (melting point=65° to 68° C.) at a yield of 69%.

EXAMPLE 12

Preparation of methyl 2-[(4,6-dimethoxypyrimidin-2-yl)oxy]-6-[1-(N-ethoxyimino)ethyl]benzoate (Compound No. 11)

1.0 g of methyl 2-acetyl-6-[(4,6-dimethoxypyrimidin-2-yl)oxy]benzoate, 1.18 g of ethoxyamine hydrochloride and 1.18 g of potassium acetate were added to 30 ml of methanol, and the resultant mixture was refluxed with stirring for 5 hours. The reaction mixture was then poured into a cold water, and was extracted with ethyl acetate. The organic layer thus formed was washed with firstly dilute hydrochloric acid, then aqueous solution of sodium hydrogencarbonate and water in sequence. The organic layer was then dried and concentrated to obtain a solid. The solid product thus obtained was washed with n-hexane to obtain 0.76 g of the aimed compound (melting point=93° to 95° C.) at a yield of 67% as a colorless transparent crystal.

EXAMPLE 13

Preparation of methyl 2-[1-(N-allyloxyimino)ethyl]-6-[(4,6-dimethoxypyrimidin-2-yl]oxy]benzoate (Compound No. 14)

1.0 g of methyl 2-acetyl-6-[(4,6-dimethoxypyrimidin-2-yl)oxy]benzoate, 1.0 g of allyloxyamine hydrochloride and 0.9 g of potassium acetate were added to 30 ml of methanol, and were refluxed with stirring for 5 hours. The reaction mixture was then poured into a cold water, and was extracted with ethyl acetate. The organic layer thus formed was washed with firstly dilute hydrochloric acid, then sodium hydrogencarbonate and water in sequence. The organic layer thus washed was then dried and concentrated. The residue oily product was purified by column chromatography to obtain 0.54 g of the aimed compound (melting point=76° to 78° C.) at a yield of 46% as a colorless transparent crystal.

REFERENCE EXAMPLE 5

Preparation of methyl 2-[(4,6-dimethoxypyrimidin-2-yl)oxy]-6-propionylbenzoate (Intermediate product No. 17)

0.78 g of 3-hydroxy-2-methoxycarbonylpropiophenone and 0.85 g of 2-methylsulfonyl-4,6-dimethoxypyrimidine were dissolved in 60 ml of DMF (dimethylformamide), and 0.15 g of sodium hydride (60% oil dispersion) was added thereto under cooling with ice. The resultant mixture was stirred at room temperature for 8 hours, and an ice water was added thereto. The resultant reaction liquor was extracted with ethyl acetate, and the extracted product was washed with a saturated salt aqueous solution, and was dried with magnesium sulfate anhydride. After distilling off the solvent, the mixture was purified by column chromatography, and was crystallized with isopropyl ether to obtain 0.92 g of the aimed compound (melting point=120° to 122° C.) at a yield of 71.3%.

EXAMPLE 14

Preparation of methyl 6-[1-(N-methoxyimino)propyl]-2-[(4,6-dimethoxypyrimidin-2-yl)oxy]benzoate (Compound No. 53)

0.62 g of methyl 2-[(4,6-dimethoxypyrimidin-2-yl)oxy]-6-propionylbenzoate, 0.45 g of methoxyamine hydrochloride and 0.53 g of potassium acetate were added to 80 ml of methanol, and were heat-refluxed for 6 hours.

The precipitated product was filtered out, and the solvent was distilled off. Water was added to the product, and the product was extracted with ethyl acetate. The product was then washed with water, and was dried with magnesium sulfate anhydride. After distilling off the solvent, the mixture was purified by column chromatography, and the purified product was crystallized with isopropyl ether/ethyl acetate to obtain 0.60 g of the aimed compound (melting point=75° to 77° C.) at a yield of 89.5%.

EXAMPLE 15

Preparation of methyl 2-[(4,6-dimethoxypyrimidin-2-yl]-N-formylamino-6-[1-[N-methoxyimino)ethyl]benzoate (Compound No. 131)

10 g of methyl 2-formylamino-6-[1-(N-methoxyimino)ethyl]benzoate was added to a solution of 1.68 g of sodium hydride in 100 ml of benzene, and the resultant mixture was stirred at room temperature for 10 minutes. 8.7 g of 2-methylsulfonyl-4,6-dimethoxypyrimidine was added to the resultant mixture, and the mixture was heat-refluxed for 6 hours. After allowing to cool, the reaction liquor was poured into an ice water, and was extracted with ethyl acetate. The organic layer thus formed was washed with water, dried and concentrated. The residue thus obtained was purified by column chromatography to obtain 8.3 g of the aimed compound (melting point=147° to 149° C.) at a yield of 54%.

EXAMPLE 16

Preparation of methyl 2-[(4,6-dimethoxypyrimidin-2-yl)amino]-6-[1-(N-methoxyimino)ethyl]benzoate (Compound No. 46)

1 ml of concentrated hydrochloric acid was added to a solution of 1.34 g of methyl 2-[(4,6-dimethoxypyrimidin-2-yl)-N-formylamino]-6-[1-(N-methoxyimino)ethyl]benzoate in 50 ml of methanol, and the mixture was allowed to stand at room temperature for one night. The reaction liquor was poured into an ice water, and was extracted with ethyl acetate. The organic layer thus formed was washed with sodium hydrogencarbonate aqueous solution and water in sequence, and was dried and concentrated. The residue thus obtained was purified by column chromatography to obtain 0.87 g of the aimed compound (melting point=82° to 84° C.) at a yield of 70%.

The herbicidal composition of the present invention comprises the pyrimidine or triazine derivative of the present invention of the general formula [I] and its salt as an effective ingredient.

When the compound of the present invention is applied as a herbicide to paddy field, upland field, fruit garden, non-agricultured land or the like, the effective ingredient may be applied in various formulations depending on its use object.

Generally, the herbicide of the present invention may be used as it is or may be formulated in various formulations which are commonly used as herbicidal compositions, such as a wettable powder, a granule, an emulsifiable concentrate or a dust by blending it with an inert liquid or solid carrier, a surfactant, a dispersing agent or an adjuvant which is commonly employed for the formulation of agricultural chemicals.

As the carrier to be used for the formulation, there may be mentioned a solid carrier such as Jeeklight, talc, bentonite, clay, kaolin, diatomaceous earth, white carbon, vermiculite, slaked lime, silica sand, ammonium sulfate or urea, or a liquid carrier such as isopropyl alcohol, xylene, cyclohexanone or methyl naphthalene. As the surfactant and dispersing agent, there may be mentioned, for example, an alcohol-sulfuric acid ester, an alkylaryl sulfonate, lignin sulfonate, a polyoxyethylene glycol ether, a polyoxyethylene alkyl aryl ether or a polyoxyethylene sorbitol mono-alkylate. As the adjuvant, for example, carboxymethylcellulose, polyethylene glycol or gum arabic may be mentioned. The herbicide may be diluted to a suitable concentration before application, or may directly be applied.

The compound of the present invention is generally used in an amount of 1 g to 10 kg/ha, preferably 1 g to 5 kg/ha, more preferably 10 g to 500 g/ha as an active ingredient.

The proportion of the compound of the present invention in the formulation may vary depending upon the type of the formulation, the application method, the application site, timing, etc. Therefore, it can not generally be defined. However, it is usually from 1 to 50%, preferably 10 to 20% by weight in a wettable powder, from 0.1 to 90%, preferably 0.5 to 40% by weight in an emulsifiable concentrate, from 0.01 to 10%, preferably 0.1 to 1% by weight in a granule.

The herbicide is capable of controlling various weeds in a paddy field by irrigated soil treatment before or after the emergence of weeds or by foliage treatment.

Further, the herbicide of the present invention is capable of controlling various weeds in an agricultural field such as an upland field or an orchard, or in a forest, a lawn or other non-agricultural field by soil treatment before or after the emergence of weeds or by foliage treatment.

For soil treatment, the herbicide of the present invention is applied in a dose of from 1 g to 10 kg, preferably from 1 g to 5 kg, more preferably from 10 g to 500 g, of the active ingredient per ha. For foliage treatment, it is diluted to a concentration of from 1 to 10,000 ppm for application. Most preferably, it is applied in a dose of from 10 to 100 g of the active ingredient per ha for a paddy field, in a dose of from 500 g to 1 kg for a non-agricultured field.

If desired, the compound of the present invention may be used in combination with insecticides, sterilizers, other herbicides, plant growth controlling agents, fertilizers or the like.

Examples of other known herbicides usable in combination with the compound of the present invention include 4-nitrophenyl 2,4,6-trichlorophenyl ether (chlornitrofen), 2,4-dichlorophenyl 3-methoxy-4-nitrophenyl ether (chlomethoxynil), methyl 5-(2,4-dichlorophenoxy)-2-nitrobenzoate (bifenox), S-4-chlorobenzyl diethylthiocarbamate (thiobencarb), S-ethyl perhydroazepin-1-carbothioate (molinate), S-1-methyl-1-phenylethyl pipperidine-1-carbothioate (dimepiperate), S-benzyl-N-(1,2-dimethylpropyl)-N-ethylthiocarbamate (esprocarb), O-(3-tert-butylphenil)N-(6-methoxy-2-pyrizyl)-N-methyl-thiocarbamate (pyributycarb), methyl 3,4-dichlorophenylcarbamate (swep), O,O-diisopropyl S-(2-phenylsulfonylaminoethyl)phosphorodithioate (bensulide), S-2-methylpiperidinocarbonylmethyl O,O-dipropyl phosphorodithioate (piperophos), N-(butoxymethyl)-2-chloro-2',6'-diethylacetanilide (butachlor), 2-chloro-2',6'-diethyl-N-(2-propoxyethyl)acetanilide (pretilachlor), 2-(benzothiazol-2-yloxy)-N-methylacetanilide (mefenacet), (RS)-2-bromo-3,3-dimethyl-N-(α,α-dimethylbenzyl)butyramide (bromobutide), (2,4-dichlorophenoxy)acetic acid (2,4-D) and 2,4-D ethyl ester, 4-chloro-o-tolyloxyacetic acid (MCPA) and MCPA ethyl ester, S-ethyl 4-chloro-o-tolyloxythioacetate (MCPA-thioethyl), 4-(4-chloro-o-tolyloxy)butyric acid (MCPB), 2-(2-naphthyloxy)propionanilide (naproanilide), 2-(22,4-dichloro-3-methylphenoxy)propionanilide (clomeprop), 2-(1,2-dimethylpropylamino)-4 ethylamino-6-methylthio-1,3,5-triazine (dimethametryn), 2,4-bis(ethylamino)-6-methylthio-1,3,5 triazine (simetryn), 2,4-bis(isopropylamino)-6-methylthio-1,3,5-triazine (prometryn), 1-($\alpha,\alpha$-dimethylbenzyl)-3 (p-tolyl)urea (dymrone), 5-tert-butyl-3-(2,4-dichloro-5-isopropoxyphenyl)-1,3,4-oxadiazole-2(3H)-one (oxadiazon), 4-(2,4-dichlorobenzoil)-1,3-dimethyl-5-pyrazolyl p-toluenesulfonate (pyrazolate), 2-[4-(2,4-dichloro-3-methylbenzoil)-1,3-dimethylpyrazol-5-yloxy]-4-methylacetophenone (benzofenap), 2-[4-(2,4-dichlorobenzoil-1,3-dimethylpyrazol-5-yloxy)acetophenon (pyrazoxyfen), 3-isopropyl-1H-2,1,3-benzothiadiazine-4(3H)-one 2,2-dioxide (bentazone), methyl 2-[[[(4,6-dimethoxypyrimidin-2-yl)aminocarbonyl]aminosulfonyl]methyl]benzoate (bensulfuron-methyl), ethyl-5-[3-(4,6-dimethoxypyrimidin-2-yl)ureidesulfonyl]-1-methylpyrazol-4-carboxylate (pyrazosulfuron-ethyl) and the like.

Now, Formulation Examples for the herbicidal composition of the present invention will be given. However, it should be understood that the present invention is by no means restricted to these specific Formulation Examples. In this Examples, "part" means "part by weight".

FORMULATION EXAMPLE 1 (WETTABLE POWDER)

10 Parts of Compound No. 11, 0.5 part of Emulgen 810 (trademark, Kao Corporation), 0.5 part of Demol N (trademark, Kao Corporation), 20 parts of Kunilite 201 (trademark, Kunimine Kogyo K. K.) and 69 parts of Jeeklite CA (trademark, Jeeklite Company Ltd.) were uniformly mixed and pulverized to obtain a wettable powder.

FORMULATION EXAMPLE 2 (WETTABLE POWDER)

10 Parts of Compound No. 14, 0.5 part of Emulgen 810, 0.5 part of Demol N, 20 parts of Kunilite 201, 5 parts of Carplex 80 and 64 parts of Jeeklite CA were uniformly mixed and pulverized to obtain a wettable powder.

FORMULATION EXAMPLE 3 (EMULSIFIABLE CONCENTRATE)

30 Parts of Compound No. 1, 60 parts of equivalent amount mixture of xylene and isophorone, and 10 parts of surface active agent Sorpol 800A (trademark, Toho Kagaku Kogyo K. K.) were uniformly mixed and stirred to obtain an emulsifiable concentrate.

FORMULATION EXAMPLE 4 (GRANULE)

10 Parts of Compound No. 9, 80 parts of a bulking agent comprising a 1:3 mixture of talc and bentonite, 5 parts of white carbon, 5 parts of surface active agent Sorpol 800A and 10 parts of water were fully kneaded to obtain a paste-like material. The paste-like material was then extruded through a sieve aperture of 0.7 mm in diameter, and the extruded product was dried and cut into pieces of 0.5 to 1 mm in length to obtain granules.

FORMULATION EXAMPLE 5 (MIXED GRANULES)

2 Parts of Compound NO. 9, 5 parts of bensulfuron-methyl, 80 parts of a bulking agent comprising a 1:3 mixture of talc and bentonite, 5 parts of white carbon, 5 parts of surface active agent Sorpol 800A and 10 parts of water were fully kneaded to obtain a paste-like material which was then extruded through a sieve aperture of 0.7 mm in diameter, dried and cut into pieces of 0.5 to 1 mm in length to obtain granules.

The compound of the present invention expressed by the general formula [I] achieves an excellent herbicidal effect at a very small dose during a long period of time from budding to growing of annual weeds such as barnyardgrass (*Echinochloa crusgalli*), flatsedge (*Cyperus diformis*), monochoria (*Monochoria vaginalis*) or the like, and perennial weeds such as bulrush (*Scirpus hotarui*), *Alisma canaliculatum*, *Sagittaria pygmaea*, *Cyperus serotinus*, *Eleocharis kuroguwai* or the like grown in paddy field. The compound of the present invention is also effective as a herbicide for various weeds such as broad leaf weeds including pale smartweed (*Polygonum lapathifolium*), slender amaranth (*Amaranthus viridis*), lambsquarters (*Chenopodium album*), chickweed (*Stellaria media*), velvetleaf (*Abutilon theophrasti*), prickly sida (*Sida spinosa*), morningglory (*Ipomea spp*), common cocklebur (*Xanthium strumarium*) or the like, perennial and annual yellow nutsedge family weeds including purple nutsedge (*Cyperus rotundus*), yellow nutsedge (*Cyperus esculentus*), green kyllinga (*Cyperus brevifolius*), flatsedge (*Cyperus microiria*), rice flatsedge (*Cyperus iria*) or the like, rice family weeds including barnyardgrass (*Echinochloa crusgalli*), crabgrass (*Digitaria sanguinalis*), green foxtail (*Setaria viridis*), annual bluegrass (*Poa annua*), johnsongrass (*Sorghum halepense*), water foxtail (*Alopecurus aequalis*), wild oat (*Avena fatua*) or the like.

On the other hand, the herbicides of the present invention are highly safe to crop plants, particularly rice, wheat, barley, corn, grain sorghum, soybean, cotton, sugar beet or the like.

Now, the herbicidal activities of the present invention will be described with reference to Test Examples.

TEST EXAMPLE 1 (HERBICIDAL EFFECT TEST BY PADDY FIELD SOIL TREATMENT)

In a plastic pot filled with paddy field soil (surface area: 100 cm$^2$), seeds of barnyardgrass (Ec), monochoria (Mo) and Bulrush (Sc) were sown after puddling and leveling, and water was flooded thereon to a depth of 3 cm. Next day, a wettable powder prepared in accordance with Formulation Example 1 was diluted with water, and was applied to dropwise to the pot in an amount of 1 kg/ha as an active ingredient. Then, the pot was cultured in a green house, and the evaluation was conducted on the 21st day after the treatment in accordance with the standard as identified in the following Table 3-1. The results are shown in the following Table 4.

TABLE 3-1

| Index No. | Herbicidal effects |
|---|---|
| 0 | Herbicidal effect: more than 0% and less than 10% |
| 1 | Herbicidal effect: at least 10% and less than 30% |
| 2 | Herbicidal effect: at least 30% and less than 50% |
| 3 | Herbicidal effect: at least 50% and less than 70% |
| 4 | Herbidadal effect: at least 70% and less than 90% |

TABLE 3-1-continued

| Index No. | Herbicidal effects |
|---|---|
| 5 | Herbicidal effect: at least 90% |

TABLE 3-2

| Index No. | Phytotoxicity |
|---|---|
| 0 | Phytotoxicity: more than 0% and less than 10% |
| 1 | Phytotoxicity: at least 10% and less than 30% |
| 2 | Phytotoxicity: at least 30% and less than 50% |
| 3 | Phytotoxicity: at least 50% and less than 70% |
| 4 | Phytotoxicity: at least 70% and less than 90% |
| 5 | Phytotoxicity: at least 90% to completely withered |

TABLE 4

| Compound No. | Herbicidal effect | | |
|---|---|---|---|
| | Ec | Mo | Sc |
| 1 | 5 | 5 | 5 |
| 2 | 5 | 5 | 5 |
| 3 | 5 | 5 | 5 |
| 4 | 5 | 5 | 5 |
| 5 | 5 | 5 | 5 |
| 8 | 5 | 5 | 5 |
| 9 | 5 | 5 | 5 |
| 10 | 5 | 5 | 5 |
| 11 | 5 | 5 | 5 |
| 13 | 5 | 5 | 4 |
| 18 | 5 | 5 | 5 |
| 19 | 5 | 5 | 5 |
| 20 | 5 | 5 | 5 |
| 21 | 5 | 5 | 5 |
| 22 | 5 | 5 | 4 |
| 23 | 5 | 5 | 4 |
| 29 | 5 | 5 | 5 |
| 33 | 5 | 5 | 5 |
| 34 | 5 | 5 | 4 |
| 35 | 5 | 5 | 5 |
| 42 | 5 | 5 | 5 |
| 43 | 5 | 5 | 4 |
| 44 | 5 | 5 | 4 |
| 45 | 5 | 5 | 5 |
| 48 | 5 | 5 | 5 |
| 49 | 5 | 5 | 5 |
| 50 | 5 | 5 | 5 |
| 51 | 5 | 5 | 5 |
| 52 | 5 | 5 | 5 |
| 53 | 5 | 5 | 5 |
| 58 | 5 | 5 | 5 |
| 60 | 5 | 5 | 4 |
| 61 | 5 | 5 | 5 |
| 62 | 5 | 5 | 4 |
| 63 | 5 | 5 | 5 |
| 64 | 5 | 5 | 5 |
| 65 | 5 | 5 | 5 |
| 67 | 5 | 5 | 5 |
| 68 | 5 | 5 | 5 |
| 69 | 5 | 5 | 5 |
| 70 | 5 | 5 | 5 |
| 71 | 5 | 5 | 5 |
| 72 | 5 | 5 | 5 |
| 73 | 5 | 5 | 5 |
| 74 | 5 | 5 | 5 |
| 75 | 5 | 5 | 5 |
| 76 | 5 | 5 | 5 |
| 78 | 5 | 5 | 5 |
| 79 | 5 | 5 | 5 |
| 80 | 5 | 5 | 5 |
| 81 | 5 | 5 | 5 |
| 82 | 5 | 5 | 5 |
| 83 | 5 | 5 | 5 |
| 84 | 5 | 5 | 5 |
| 85 | 5 | 5 | 5 |
| 86 | 5 | 5 | 5 |
| 87 | 5 | 5 | 5 |
| 88 | 5 | 5 | 5 |
| 91 | 5 | 5 | 5 |
| 92 | 5 | 5 | 5 |
| 93 | 5 | 5 | 5 |
| 118 | 5 | 5 | 5 |
| 119 | 5 | 5 | 5 |
| 120 | 5 | 5 | 5 |
| 121 | 5 | 5 | 5 |
| 129 | 5 | 5 | 5 |
| 130 | 5 | 5 | 5 |
| 136 | 5 | 5 | 5 |
| 137 | 5 | 5 | 5 |

TEST EXAMPLE 2 (HERBICIDAL EFFECT TEST BY UPLAND FIELD SOIL TREATMENT)

In a plastic pot filled with upland field soil (surface area: 120 cm$^2$), seeds of edible barnyardgrass (Ec), pale smartweed (Po), Slender amaranth (Am), Lambsquarters (Ch) and rice flatsedge (Cy) were sown and covered with soil. A predetermined amount of a wettable powder prepared in accordance with Formulation Example 1 was diluted with water and applied uniformly to the soil surface by a small-sized sprayer in an amount of 1000 l/ha so that the dose of the active ingredient was 1 kg/ha. The pot was then cultured in a green house, and the evaluation was conducted on the 21st day after the treatment in accordance with the standard as identified in the following Table 3-1. The compounds listed in the following Table 5 were used as comparative herbicides. The test results are shown in the following Table 6.

TABLE 5

| Chemical structure | Reference |
|---|---|
| (A) 3-chlorophenyl-O-C(=N-C(CH$_3$)=CH-C(CH$_3$)=N) pyrimidine | U.S. Pat. No. 4770691 |
| (B) 2,6-dichlorophenyl-O-C(=N-C(CH$_3$)=CH-C(CH$_3$)=N) pyrimidine | Agricultural and Biological Chemistry 30,9,896, (1966) |
| (C) 2-(COOC$_3$H$_7$-i)phenyl-O-C(=N-C(OCH$_3$)=CH-C(OCH$_3$)=N) pyrimidine | U.S. Pat. No. 4427437 |

TABLE 6

| Compound No. | Herbicidal effect | | | | |
|---|---|---|---|---|---|
| | Ec | Po | Am | Ch | Cy |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |

TABLE 6-continued

| Compound No. | Herbicidal effect | | | | |
|---|---|---|---|---|---|
| | Ec | Po | Am | Ch | Cy |
| 7 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| 14 | 5 | 5 | 5 | 5 | 5 |
| 15 | 5 | 5 | 5 | 5 | 5 |
| 16 | 5 | 5 | 5 | 5 | 5 |
| 17 | 5 | 5 | 5 | 5 | 5 |
| 18 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 24 | 4 | 5 | 5 | 5 | 5 |
| 29 | 5 | 5 | 5 | 5 | 5 |
| 30 | 4 | 5 | 5 | 5 | 5 |
| 32 | 5 | 5 | 5 | 5 | 5 |
| 33 | 5 | 5 | 5 | 5 | 5 |
| 34 | 5 | 5 | 5 | 5 | 5 |
| 35 | 5 | 5 | 5 | 5 | 5 |
| 42 | 5 | 5 | 5 | 5 | 5 |
| 43 | 5 | 5 | 5 | 5 | 5 |
| 44 | 5 | 5 | 5 | 5 | 5 |
| 45 | 5 | 5 | 5 | 5 | 5 |
| 48 | 5 | 5 | 5 | 5 | 5 |
| 49 | 5 | 5 | 5 | 5 | 5 |
| 50 | 5 | 5 | 5 | 5 | 5 |
| 51 | 5 | 5 | 5 | 5 | 5 |
| 52 | 5 | 5 | 5 | 5 | 5 |
| 53 | 5 | 5 | 5 | 5 | 5 |
| 58 | 5 | 5 | 5 | 5 | 5 |
| 60 | 5 | 5 | 5 | 5 | 5 |
| 61 | 5 | 5 | 5 | 5 | 5 |
| 63 | 5 | 5 | 5 | 5 | 5 |
| 64 | 5 | 5 | 5 | 5 | 5 |
| 65 | 5 | 5 | 5 | 5 | 5 |
| 67 | 5 | 5 | 5 | 5 | 5 |
| 68 | 5 | 5 | 5 | 5 | 5 |
| 69 | 5 | 5 | 5 | 5 | 5 |
| 70 | 5 | 5 | 5 | 5 | 5 |
| 71 | 5 | 5 | 5 | 5 | 5 |
| 72 | 5 | 5 | 5 | 5 | 5 |
| 73 | 5 | 5 | 5 | 5 | 5 |
| 74 | 5 | 5 | 5 | 5 | 5 |
| 75 | 5 | 5 | 5 | 5 | 5 |
| 76 | 5 | 5 | 5 | 5 | 5 |
| 78 | 5 | 5 | 5 | 5 | 5 |
| 79 | 5 | 5 | 5 | 5 | 5 |
| 80 | 5 | 4 | 5 | 5 | 5 |
| 81 | 5 | 5 | 5 | 5 | 5 |
| 82 | 5 | 5 | 5 | 5 | 5 |
| 83 | 5 | 5 | 5 | 5 | 5 |
| 84 | 5 | 5 | 5 | 5 | 5 |
| 85 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 91 | 5 | 5 | 5 | 5 | 5 |
| 92 | 5 | 5 | 5 | 5 | 5 |
| 93 | 5 | 5 | 5 | 5 | 5 |
| 118 | 5 | 5 | 5 | 5 | 5 |
| 119 | 5 | 5 | 5 | 5 | 5 |
| 120 | 5 | 5 | 5 | 5 | 5 |
| 121 | 5 | 5 | 5 | 5 | 5 |
| 129 | 5 | 5 | 5 | 5 | 5 |
| 130 | 5 | 5 | 5 | 5 | 5 |
| 136 | 5 | 5 | 5 | 5 | 5 |
| (A) | 3 | 4 | 4 | 5 | 5 |
| (B) | 1 | 0 | 3 | 2 | 1 |
| (C) | 2 | 3 | 5 | 5 | 0 |

TEST EXAMPLE 3 (HERBICIDAL EFFECT TEST BY UPLAND FIELD FOLIAGE TREATMENT)

In a plastic pot filled with upland soil (surface area: 120 cm$^2$), seeds of edible barnyardgrass (Ec), pale smartweed (Po), slender amaranth (Am), lambsquarters (Ch) and rice flatsedge (Cy) were sown, and were cultured in a green house for 2 weeks. A predetermined amount of a wettable powder prepared in accordance with Formulation Example 1 was diluted with water, and applied by a small-sized sprayer onto the foliage in an amount of 1000 l/ha so that the dose of the active ingredient was 1 kg/ha. The plants were cultured in the green house, and the evaluation was conducted on the 14th day after the treatment in accordance with the standard as identified in the following Table 3-1. The compounds listed in the above Table 5 were used as comparative herbicides. The test results are shown in the following Table 7.

TABLE 7

| Compound No. | Herbicidal effect | | | | |
|---|---|---|---|---|---|
| | Ec | Po | Am | Ch | Cy |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |
| 7 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 4 | 5 | 5 | 5 |
| 14 | 5 | 5 | 5 | 5 | 5 |
| 15 | 5 | 5 | 5 | 5 | 5 |
| 16 | 5 | 5 | 5 | 5 | 5 |
| 17 | 5 | 5 | 5 | 5 | 5 |
| 18 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 24 | 4 | 5 | 5 | 5 | 4 |
| 29 | 5 | 5 | 5 | 5 | 5 |
| 30 | 5 | 5 | 5 | 5 | 5 |
| 33 | 5 | 5 | 5 | 5 | 5 |
| 35 | 5 | 5 | 5 | 5 | 5 |
| 42 | 5 | 5 | 5 | 5 | 5 |
| 43 | 5 | 5 | 5 | 5 | 5 |
| 44 | 5 | 5 | 5 | 5 | 5 |
| 45 | 5 | 5 | 5 | 5 | 5 |
| 48 | 5 | 5 | 5 | 5 | 5 |
| 49 | 5 | 5 | 5 | 5 | 5 |
| 51 | 5 | 5 | 5 | 5 | 5 |
| 52 | 5 | 5 | 5 | 5 | 5 |
| 58 | 5 | 5 | 5 | 5 | 4 |
| 60 | 5 | 5 | 5 | 5 | 4 |
| 61 | 5 | 5 | 5 | 5 | 4 |
| 63 | 5 | 5 | 5 | 5 | 5 |
| 64 | 5 | 5 | 5 | 5 | 5 |
| 65 | 5 | 5 | 5 | 5 | 5 |
| 67 | 5 | 5 | 5 | 5 | 5 |
| 68 | 5 | 5 | 5 | 5 | 5 |
| 69 | 5 | 5 | 5 | 5 | 5 |
| 70 | 5 | 5 | 5 | 5 | 5 |
| 71 | 5 | 5 | 5 | 5 | 5 |
| 72 | 5 | 5 | 5 | 5 | 5 |
| 73 | 5 | 5 | 5 | 5 | 5 |
| 74 | 5 | 5 | 5 | 5 | 5 |
| 75 | 5 | 5 | 5 | 5 | 5 |
| 76 | 5 | 5 | 5 | 5 | 5 |
| 78 | 5 | 5 | 5 | 5 | 5 |
| 79 | 5 | 5 | 5 | 5 | 5 |

TABLE 7-continued

| Compound No. | Herbicidal effect | | | | |
|---|---|---|---|---|---|
| | Ec | Po | Am | Ch | Cy |
| 80 | 5 | 4 | 5 | 5 | 5 |
| 81 | 5 | 5 | 5 | 5 | 5 |
| 82 | 5 | 5 | 5 | 5 | 5 |
| 83 | 5 | 5 | 5 | 5 | 5 |
| 84 | 5 | 5 | 5 | 5 | 5 |
| 85 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 91 | 5 | 5 | 5 | 5 | 5 |
| 92 | 5 | 5 | 5 | 5 | 5 |
| 93 | 5 | 5 | 5 | 5 | 5 |
| 118 | 5 | 5 | 5 | 5 | 5 |
| 119 | 5 | 5 | 5 | 5 | 5 |
| 120 | 5 | 5 | 5 | 5 | 5 |
| 121 | 5 | 5 | 5 | 5 | 5 |
| 129 | 5 | 5 | 5 | 5 | 5 |
| 130 | 5 | 5 | 5 | 5 | 5 |
| 136 | 5 | 5 | 5 | 5 | 5 |
| (A) | 1 | 3 | 1 | 3 | 5 |
| (B) | 0 | 0 | 0 | 0 | 0 |
| (C) | 2 | 3 | 5 | 5 | 0 |

TEST EXAMPLE 4 (CROP SELECTIVITY TEST BY PADDY FIELD SOIL TREATMENT)

In a Wagner pot (surface area: 1/5000 a) filled with paddy field soil, barnyardgrass (Ec), monochoria (Mo) and bulrush (Sc) were sown after irrigating, puddling and leveling. In the pot, two pieces of paddy rice (Or) of 2.0 plastochron were transplanted to a transplanting depth of 2 cm, and flooded to a water depth of 3 cm. Next day, a predetermined amount of a wettable powder prepared in accordance with Formulation Example 1 diluted with water, and applied dropwise to the water surface. The plants were then cultured in a green house, and the evaluations of the herbicidal effect and phytotoxicity were conducted on the 30th day after the treatment in accordance with the standards as identified in Tables 3-1 and 3-2. The compounds listed in the above Table 5 were used as comparative herbicides. The results are shown in the following Table 8.

TABLE 8

| Compound No. | Dose (kg/ha) | Herbicidal effect | | | Phytotoxicity |
|---|---|---|---|---|---|
| | | Ec | Mo | Sc | Or |
| 4 | 0.25 | 5 | 3 | 3 | 1 |
| 5 | 1.00 | 5 | 5 | 5 | 1 |
| 9 | 0.25 | 5 | 3 | 3 | 0 |
| 10 | 0.25 | 5 | 3 | 3 | 0 |
| 11 | 0.25 | 5 | 4 | 3 | 1 |
| 13 | 1.00 | 5 | 5 | 3 | 1 |
| 20 | 0.25 | 5 | 5 | 4 | 1 |
| 21 | 0.25 | 5 | 4 | 4 | 0 |
| 23 | 0.25 | 5 | 5 | 3 | 0 |
| 30 | 1.00 | 5 | 5 | 3 | 1 |
| 33 | 1.00 | 5 | 5 | 5 | 1 |
| 35 | 0.25 | 5 | 5 | 3 | 0 |
| 43 | 0.25 | 5 | 5 | 3 | 0 |
| 50 | 1.00 | 5 | 5 | 5 | 0 |
| 62 | 0.25 | 5 | 5 | 3 | 0 |
| 78 | 0.25 | 5 | 5 | 5 | 0 |
| 79 | 0.25 | 5 | 5 | 5 | 0 |
| 80 | 0.25 | 5 | 5 | 5 | 0 |
| 91 | 1.00 | 5 | 5 | 5 | 0 |
| 93 | 1.00 | 5 | 5 | 5 | 0 |
| (A) | 1.00 | 0 | 0 | 0 | 2 |
| (B) | 1.00 | 0 | 0 | 0 | 0 |
| (C) | 1.00 | 5 | 5 | 3 | 5 |

TEST EXAMPLE 5 (CROP SELECTIVITY TEST BY UPLAND FIELD SOIL TREATMENT)

In a plastic pot (surface area: 600 cm$^2$) filled with upland field soil, soybean (Gl), cotton (Go), edible barnyardgrass (Ec), johnsongrass (So), water foxtail (Al), pale smartweed (Po), slender amaranth (Am) and lambsquarters (Ch) were sown and covered with soil. Next day, a predetermined amount of a wettable powder prepared in accordance with Formulation Example 1 was diluted with water, and applied uniformly onto the soil surface by a small-sized sprayer in an amount of 1000 l/ha. The plants were then cultured in a green house, and the evaluations of the herbicidal effect and phytotoxicity were conducted on the 21st day after the treatment in accordance with the standards as identified in Tables 3-1 and 3-2. The compounds listed in the above Table 5 were used as comparative herbicides. The results are shown in the following Table 9.

TABLE 9

| Compound No. | Dose (kg/ha) | Herbicidal effect | | | | | | Phytotoxicity | |
|---|---|---|---|---|---|---|---|---|---|
| | | Ec | So | Al | Po | Am | Ch | Gl | Go |
| 4 | 0.063 | 4 | 5 | 5 | 5 | 5 | 4 | 1 | 0 |
| 9 | 0.25 | 5 | 5 | 5 | 5 | 5 | 5 | 0 | 0 |
| 10 | 0.063 | 5 | 5 | 5 | 5 | 5 | 5 | 0 | 1 |
| 11 | 0.25 | 5 | 5 | 5 | 5 | 5 | 5 | 2 | 0 |
| 20 | 0.063 | 5 | 5 | 4 | 5 | 5 | 5 | 1 | 0 |
| 21 | 0.063 | 5 | 5 | 5 | 5 | 5 | 5 | 1 | 0 |
| 33 | 0.063 | 5 | 5 | 5 | 5 | 5 | 5 | 1 | 0 |
| 34 | 0.063 | 5 | 5 | 4 | 5 | 5 | 4 | 0 | 0 |
| 50 | 0.25 | 5 | 4 | 4 | 4 | 5 | 5 | 1 | 0 |
| 51 | 0.063 | 5 | 4 | 4 | 4 | 5 | 4 | 0 | 0 |
| (A) | 0.25 | 0 | 0 | 1 | 2 | 2 | 1 | 0 | 0 |
| (B) | 0.25 | 0 | 0 | 0 | 0 | 1 | 1 | 0 | 0 |
| (C) | 0.25 | 0 | 0 | 1 | 1 | 3 | 3 | 0 | 0 |

TEST EXAMPLE 6 (CROP SELECTIVITY T FOLIAGE TREATMENT)

In a plastic pot (surface area: 600 cm$^2$) filled with upland field soil, rice (Or), cotton (Co), edible barnyardgrass (Ec), pale smartweed (Po), slender amaranth (Am) and lambsquarters (Ch) were sown and were cultured in a green house for 2 weeks. A predetermined amount of a wettable powder prepared in accordance with Formulation Example 1 was diluted with water, and applied onto the foliage by a small-sized sprayer. The plants were then cultured in the green house, and the evaluations of the herbicidal effect and phytotoxicity were conducted on the 14th day after the treatment. The compounds listed in the above Table 5 were used as comparative herbicides. The results are shown in the following Table 10.

TABLE 10

| Compound No. | Dose (kg/ha) | Herbicidal effect | | | | | | Phytotoxicity | |
|---|---|---|---|---|---|---|---|---|---|
| | | Ec | So | Al | Po | Am | Ch | Or | Go |
| 5 | 0.063 | 4 | 4 | 5 | 4 | 5 | 5 | 0 | 0 |
| 6 | 0.25 | 5 | 5 | 5 | 5 | 5 | 5 | 0 | 1 |
| 7 | 0.25 | 5 | 5 | 5 | 5 | 5 | 5 | 0 | 0 |
| 12 | 0.063 | 5 | 5 | 4 | 5 | 5 | 5 | 0 | 2 |
| 13 | 0.25 | 5 | 5 | 5 | 5 | 5 | 5 | 0 | 1 |
| 14 | 0.063 | 5 | 5 | 5 | 5 | 5 | 5 | 0 | 0 |
| 33 | 0.25 | 5 | 4 | 5 | 5 | 5 | 5 | 1 | 0 |
| 52 | 0.063 | 4 | 5 | 5 | 5 | 5 | 5 | 1 | 1 |
| (A) | 0.25 | 3 | 2 | 0 | 4 | 2 | 1 | 0 | 2 |
| (B) | 0.25 | 0 | 0 | 0 | 0 | 0 | 1 | 1 | 0 |
| (C) | 0.25 | 1 | 0 | 0 | 1 | 3 | 3 | 1 | 1 |

TEST EXAMPLE 7 (HERBICIDAL EFFECT TEST FOR COMBINATION USE OF HERBICIDES BY PADDY FIELD SOIL TREATMENT)

In a concrete pot (surface area: 1/400 a) filled with paddy field soil, barnyardgrass (Ec), monochoria (Mo), bulrush (Sc), flatsedge (Cy) and *Lindernia pyxidaria* (Li) were sown and tubers of *Sagittaria pygmaea* (Sa) and *Cyperus serotinus* (Cs) were placed. In the pot, 8 pieces of rice (Or) of 2.0 plastochron were further transplanted to a transplanting depth of 2 cm, and flooded to a water depth of 4 cm. Next day, a predetermined amount of mixed granules prepared in accordance with Formulation Example 5 were uniformly applied thereto. The plants were then cultured outdoor, the evaluations of herbicidal effect and phytotoxicity were conducted on the 61st day after the treatment. In accordance with the standards as identified in the above Tables 3-1 and 3-2. The results are shown in the following Table 11.

TABLE 11

| Compound No. + Sample | Dose (kg/ha) | Herbicidal effect | | | | | | | Phytotoxicity |
|---|---|---|---|---|---|---|---|---|---|
| | | Ec | Mo | Sc | Cy | Li | Sa | Cs | Or |
| Compound No. 9 + bensulfronmethyl | 0.02 + 0.05 | 5 | 5 | 5 | 5 | 5 | 5 | 4 | 0 |
| | 0.04 + 0.1 | 5 | 5 | 5 | 5 | 5 | 5 | 5 | 0 |

What is claimed is:

1. A compound of the formula:

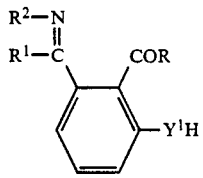

wherein

R represents a group of the formula $OR^3$;

where $R^3$ represents a hydrogen atom; a $C_{1-8}$ alkyl group which may be substituted with a halogen atom, a nitro group, a cyano group a $C_{1-8}$ alkoxy group, a $C_{1-8}$ alkylthio group, a $C_{1-8}$ alkylsulfinyl group, a $C_{1-8}$ alkylsulfonyl group, a phenylsulfinyl group, a phenylsulfonyl group, a benzyloxy group, R' CO— group wherein R'=$C_{1-8}$ alkyl, a $C_{1-8}$ alkoxycarbonyloxy group, an N,N-di-$C_{1-4}$ alkylamino group or a phthalimidoyl group; a $C_{2-8}$ alkenyl group; a halogen-substituted $C_{2-8}$ alkenyl group; a $C_{2-8}$ alkynyl group; a halogen-substituted $C_{2-8}$ alkynyl group; a phenyl group which may be substituted with a halogen atom, a $C_{1-6}$ alkyl group or a $C_{1-6}$ alkoxy group; a benzyl group which may be substituted with a halogen atom, a $C_{1-8}$ alkyl group or a $C_{1-8}$ alkoxy group; a $C_{1-4}$ alkylideneamino group; a $C_{4-6}$ cycloalkylideneamino group; a group of the formula

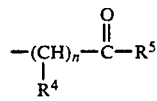

wherein $R^4$ represents a hydrogen atom or a $C_{1-3}$ alkyl group; $R^5$ represents a $C_{1-8}$ alkyl group; a phenyl group which may be substituted with a halogen atom, a $C_{1-6}$ alkyl group or a $C_{1-6}$ alkoxy group; an amino group; a $C_{1-8}$ alkylamino group or a di-$C_{1-4}$ alkylamino group; and n represents an integer of 1 to 3;

or $R^3$ represents an alkali metal atom; an alkaline earth metal atom or an organic amine cation;

or R represents a group of the formula $SR^6$; wherein $R^6$ represents a hydrogen atom; a $C_{1-8}$ alkyl group; a phenyl group which may be substituted with a halogen atom, a $C_{1-6}$ alkyl group; a benzyl group which may be substituted with a halogen atom, a $C_{1-6}$ alkyl group or a $C_{1-6}$ alkoxy group; a $C_{2-8}$ alkenyl group; a halogen-substituted $C_{2-8}$ alkenyl group; a $C_{2-8}$ alkynyl group or a halogen-substituted $C_{2-8}$ alkyl group;

or R represents a group of the formula

wherein $R^7$ and $R^8$ may be the same or different and represents a hydrogen atom; a $C_{1-8}$ alkyl group; a $C_{1-8}$ alkoxy group or a phenyl group which may be substituted with a halogen atom, a $C_{1-6}$ alkyl group or a $C_{1-6}$ alkoxy group;

or R represents an imidazolyl group; $R^1$ represents a $C_{1-8}$ alkyl group which may be substituted with a halogen atom, a $C_{1-8}$ alkoxy group, a $C_{1-8}$ alkylthio group, A $C_{1-8}$ alkylsulfinyl group, a $C_{1-8}$ alkylsulfonyl group, R"CO— group wherein R"=$C_{1-6}$ alkyl, phenyl or benzyl, or a cyano group; a phenyl group which may be substituted with a halogen atom, a $C_{1-6}$ alkyl group or a $C_{1-6}$ alkoxy group; or a benzyl group which may be substituted with a halogen atom, a $C_{1-6}$ alkyl group or a $C_{1-6}$ alkoxy group; $R^2$ represents a hydroxyl group; a $C_{1-8}$ alkyl group which may be substituted with one or two halogen atom; a $C_{2-8}$ alkoxyalkyl group; a $C_{2-8}$ alkenyl group; a $C_{2-8}$ alkynyl group; a $C_{1-8}$ alkoxy group which may be substituted with a halogen atom, a benzyloxy group, a $C_{1-8}$ alkoxycarbonyl group, a $C_{3-7}$ cycloalkyl group, a R"CO— group wherein R"=$C_{1-6}$ alkyl, phenyl or benzyl, an N,N-di $C_{1-4}$ alkylamino group or a $C_{1-8}$ alkoxy group; a phenyl group which may be substituted with a halogen atom, a $C_{1-4}$ alkyl group or a $C_{1-4}$ alkoxy group; a phenoxy group which may be substituted with a halogen atom, a $C_{1-4}$ alkyl group or a $C_{1-4}$ alkoxy group; a $C_{2-8}$ alkenyloxy group which may be substituted with one or two halogen atoms or a phenyl group; a benzyloxy group which may be substituted with a halogen atom, a $C_{1-4}$ alkyl group or a $C_{1-4}$ alkoxy group; a trimethylsilyloxy group; a $C_{3-7}$ cycloalkoxy group; a group of the formula

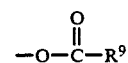

wherein $R^9$ represents an alkyl group which may be substituted with a halogen atom; a $C_{3-7}$ cycloalkyl group; a phenyl group which may be substituted with a halogen atom, a $C_{1-4}$ alkyl group or a $C_{1-4}$ alkoxy group; a $C_{1-8}$ alkoxy group or a group of the formula:

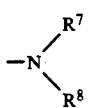

wherein $R^7$ and $R^8$ are as defined above; a group of the formula

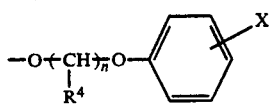

wherein X represents a halogen atom, a $C_{1-4}$ alkyl group or a $C_{1-4}$ alkoxy group, n represents an integer of 1 to 3 and $R^4$ is as defined above; a phenylamino group, a $C_{1-4}$ alkoxycarbonylamino group or a $C_{1-4}$ alkylcarbonylamino group; and $Y^1$ is an oxygen atom or a sulfur atom.

2. A compound of the formula

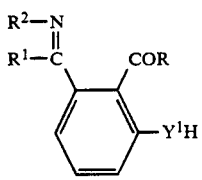

wherein
R represents a group of the formula $OR^3$;
where $R^3$ represents a hydrogen atom; a $C_{1-8}$ alkyl group which may be substituted with a halogen atom, a nitro group, a cyano group, a $C_{1-8}$ alkoxy group, a $C_{1-8}$ alkylthio group, a $C_{1-8}$ alkylsulfinyl group, a $C_{1-8}$ alkylsulfonyl group, a phenylsulfinyl group, a phenylsulfonyl group, a benzyloxy group, R'CO— group wherein $R'=C_{1-8}$ alkyl, a $C_{1-8}$ alkoxycarbonyloxy group, an N,N-di-$C_{1-4}$ alkylamino group or a phthalimidoyl group; a $C_{2-8}$ alkenyl group; a halogen-substituted $C_{2-8}$ alkenyl group; a $C_{2-8}$ alkynyl group; a halogen-substituted $C_{2-8}$ alkynyl group; a phenyl group which maybe substituted with a halogen atom, a $C_{1-6}$ alkyl group or a $C_{1-6}$ alkoxy group; a benzyl group which may be substituted with a halogen atom, a $C_{1-8}$ alkyl group or a $C_{1-8}$ alkoxy group; a $C_{1-4}$ alkylideneamino group; a $C_{4-6}$ cycloalkylideneamino group; a group of the formula

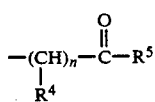

wherein $R^4$ represents a hydrogen atom or a $C_{1-3}$ alkyl group, $R^5$ represents a $C_{1-8}$ alkyl group; a phenyl group which may be substituted with a halogen atom, a $C_{1-6}$ alkyl group or a $C_{1-6}$ alkoxy group; an amino group; a $C_{1-8}$ alkylamino group or a di-$C_{1-4}$ alkylamino group; and n represents an integer of 1 to 3;
or $R^3$ represents an alkali metal atom; an alkaline earth metal atom or an organic amine cation;

or R represents a group of the formula $SR^6$; wherein $R^6$ represents a hydrogen atom; a $C_{1-8}$ alkyl group; a phenyl group which may be substituted with a halogen atom, a $C_{1-6}$ alkyl group; a benzyl group which may be substituted with a halogen atom, a $C_{1-6}$ alkyl group or a $C_{1-6}$ alkoxy group; a $C_{2-8}$ alkenyl group; a halogen-substituted $C_{2-8}$ alkenyl group; a $C_{2-8}$ alkynyl group or a halogen-substituted $C_{2-8}$ alkynyl group;
or R represents a group of the formula

wherein $R^7$ and $R^8$ may be the same or different and represents a hydrogen atom; a $C_{1-8}$ alkyl group; a $C_{1-8}$ alkoxy group or a phenyl group which may be substituted with a halogen atom, a $C_{1-6}$ alkyl group or a $C_{1-6}$ alkoxy group;
or R represents an imidazolyl group;
$R^1$ represents a $C_{1-8}$ alkyl group which may be substituted with a halogen atom, a $C_{1-8}$ alkoxy group, a $C_{1-8}$ alkylthio group, a $C_{1-8}$ alkylsulfinyl group, a $C_{1-8}$ alkylsulfonyl group, R"CO— group wherein $R''=C_{1-6}$ alkyl, phenyl or benzyl, or a cyano group; a phenyl group which may be substituted with a halogen atom, a $C_{1-6}$ alkyl group or a $C_{1-6}$ alkoxy group; or a benzyl group which may be substituted with a halogen atom, a $C_{1-6}$ alkyl group or a $C_{1-6}$ alkoxy group;
$R^2$ represents a hydroxyl group; a $C_{1-8}$ alkyl group which may be substituted with one or two halogen atom; a $C_{2-8}$ alkoxyalkyl group; a $C_{2-8}$ alkenyl group; a $C_{2-8}$ alkynyl group; a $C_{1-8}$ alkoxy group which may be substituted with a halogen atom, a benzyloxy group, a $C_{1-8}$ alkoxycarbonyl group, a $C_{3-7}$ cycloalkyl, group, a R"CO— group wherein $R''=C_{1-6}$ alkyl, phenyl or benzyl, an N,N-di-$C_{1-4}$ alkylamino group or a $C_{1-8}$ alkoxy group; a phenyl group which may be substituted with a halogen atom, a $C_{1-4}$ alkyl group or a $C_{1-4}$ alkoxy group; a phenoxy group which may be substituted with a halogen atom, a $C_{1-4}$ alkyl group or a $C_{1-4}$ alkoxy group; a $C_{2-8}$ alkenyloxy group which may be substituted with one or two halogen atoms or a phenyl group; a trimethylsilyloxy group; a $C_{3-7}$ cycloalkoxy group; a group of the formula

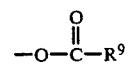

wherein $R^9$ represents an alkyl group which may be substituted with a halogen atom; a $C_{3-7}$ cycloalkyl group; a phenyl group which may be substituted with a halogen atom, a $C_{1-4}$ alkyl group or a $C_{1-4}$ alkoxy group; a $C_{1-8}$ alkoxy group or a group of the formula:

wherein $R^7$ and $R^8$ are as defined above;

a group of the formula

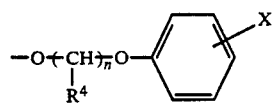

wherein X represents a halogen atom, a $C_{1-4}$ alkyl group or a $C_{1-4}$ alkoxy group, n represents an integer of 1 to 3 and $R^4$ is as defined above;
a phenylamino group, a $C_{1-4}$ alkoxycarbonylamino group or a $C_{1-4}$ alkylcarbonylamino group;
and $Y^1$ is an oxygen atom or a sulfur atom.

3. A compound of the formula

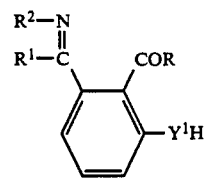

wherein R represents a $C_{1-8}$ alkoxy group or hydroxyl group; $R^1$ represents a $C_{1-8}$ alkyl group; $R^2$ represents a $C_{1-8}$ alkoxy group; $Y^1$ represents an oxygen atom or a sulfur atom.

* * * * *

UNITED STATES PATENT AND TRADEMARK OFFICE
CERTIFICATE OF CORRECTION

PATENT NO. : 5,302,739
DATED : April 12, 1994
INVENTOR(S) : Masatoshi TAMARU, et al.

It is certified that error appears in the above-indentified patent and that said Letters Patent is hereby corrected as shown below:

On the title page, Item [30], the 2nd Foreign Application Priority Date should read as follows:

--May 10, 1990--

Also, on the title page, Item [73], the 1st Assignee's name should read as follows:

--Kumiai Chemical Industry Co., Ltd.--

Signed and Sealed this

Fourth Day of October, 1994

Attest:

BRUCE LEHMAN

Attesting Officer    Commissioner of Patents and Trademarks